United States Patent
Brassell et al.

[19]

[11] Patent Number: 6,041,669
[45] Date of Patent: Mar. 28, 2000

[54] METHODS OF AND APPARATUS FOR TESTING AND VENTING DRUMS

[75] Inventors: Gilbert W. Brassell; John L. Warren, both of Lakewood; Charles E. Wickland, Tabernash; Harold Sanchez; Mark A. Castagneri, both of Lakewood, all of Colo.

[73] Assignee: NFT Incorporated, Lakewood, Colo.

[21] Appl. No.: 09/108,122

[22] Filed: Jun. 15, 1998

Related U.S. Application Data

[63] Continuation-in-part of application No. 08/725,021, Oct. 12, 1996, Pat. No. 5,767,422.

[51] Int. Cl.[7] ........................................ G01N 1/10
[52] U.S. Cl. ............................................. 73/864.74
[58] Field of Search .................... 73/52, 863.23, 73/863.33, 863.81, 863.83, 863.85, 863.86, 864.34, 864.41, 864.43, 864.73, 864.74, 864.81

[56] References Cited

U.S. PATENT DOCUMENTS

| | | |
|---|---|---|
| 3,206,982 | 9/1965 | Blondfield et al. .................. 73/864.74 |
| 3,374,678 | 3/1968 | McGuckin ........................... 73/864.74 |
| 3,412,613 | 11/1968 | Brown et al. ........................ 73/864.74 |
| 4,046,013 | 9/1977 | Green . |
| 4,493,792 | 1/1985 | Graf, Jr. . |
| 5,090,871 | 2/1992 | Story et al. . |
| 5,254,798 | 10/1993 | Zoback . |
| 5,262,578 | 11/1993 | Hall . |
| 5,767,422 | 6/1998 | Brassell et al. . |

*Primary Examiner*—Robert Raevis
*Attorney, Agent, or Firm*—Millen, White, Zelano & Branigan

[57] ABSTRACT

Transuranic waste generated at Department of Energy operations have been packaged to a large extent in unvented fifty-five gallon steel drums and have been stored with the intention of future retrieval. There are safety concerns regarding these drums because of a potential presence of hydrogen and methane generated by radiolysis of hydrogenous wastes and/or of traces of combustible volatile organic compounds contained in original waste materials. Methods and apparatus are provided for penetrating the packed drums and drum liner lids and for sampling and analyzing headspace gases as well as for purging undesirable gas mixtures and installing high efficiency particulate air filter vents. The steps of the method are performed by automated apparatus which is configured to isolate the drums having contents being tested from the surrounding environment and for inserting vents with filters concurrently with performing the tests.

22 Claims, 7 Drawing Sheets

METHODS OF AND APPARATUS FOR TESTING AND VENTING DRUMS

RELATED PATENT APPLICATIONS

This application is a continuation in part of U.S. patent application Ser. No. 08/725,021 filed Oct. 12, 1996 and assigned U.S. Pat. No. 5,767,422 to issue Jun. 16, 1998.

FIELD OF THE INVENTION

The present invention is directed to methods of and apparatus for testing and venting drums containing materials such as radioactive waste. More particularly, the present invention is directed to methods of and apparatus for testing and venting drums which may contain explosive gases or hazardous materials in association with waste materials such as radioactive waste.

BACKGROUND OF THE INVENTION

Transuranic waste material generated in the United States Department of Energy Operations have since 1970 been packaged to a large extent in unvented 55 gallon steel drums and have been stored with the intention of future retrieval. It is intended that the material in these drums will be disposed of permanently in the Department of Energy Waste Isolation Pilot Plant (WIPP) facility. Currently, there are safety concerns regarding these stored drums because of a potential presence of combustible headspace gases. These gases can include hydrogen and methane resulting from the radiolytic decomposition of hydrogenous waste materials, e.g., paper, plastics and moist materials and/or from the presence of generally small amounts of combustible volatile organic compounds (VOCs) that are co-contaminants of the transuranic wastes. Future handling and transportation of these wastes stored in drums such as 55 gallon drums must address what is to be done about such gases.

The WIPP facility has waste acceptance criteria which require that all packages stored must also be vented. Moreover, those packages which are to be shipped to the waste isolation pilot plant must both be vented and demonstrated to meet combustible gas concentration limits before shipment.

Accordingly, there is a need for methods of and apparatus for rapidly testing and venting the contents of these drums with minimal expense and inconvenience and with maximum safety.

SUMMARY OF THE INVENTION

It is a feature of the present invention to provide a safe method of and apparatus for penetrating a drum lid and a plastic inner liner lid (if present) in order to sample and analyze headspace gases and in order to install a vent filter.

In one aspect, the invention is directed to a method of testing head-space gas accumulating in the headspace of a drum. The method comprises isolating the drum from the surrounding environment by enclosing the drum in a first space and then sealing a portion of the drum's surface proximate the headspace of the drum. Access to the sealed portion of the drum's surface from a second space is provided through a third space defined by the seal. The third space defined by the seal is then closed and air is evacuated from the third space to form a vacuum therein. Using a filter cutter assembly disposed in the second space and extending through the third space, a hole is bored through the sealed surface portion of the drum to release gases from the drum into the third space. The gases are then analyzed and, if the gases are considered dangerous, purged. A filter is then installed in the hole bored through the sealed surface portion of the drum for allowing the drum to vent gases while trapping solid particles.

In another aspect, the invention is directed to apparatus for testing headspace gases in drums containing stored material. The apparatus comprises a drum containment cabinet for isolating the drum from the environment and a power head chamber above the drum containment chamber for containing a power head with a filter/cutter assembly detachably mounted thereto. A sealing assembly is provided for connecting the drum chamber to the power head chamber, the sealing assembly being aligned with the filter/cutter assembly when the filter/cutter assembly is mounted in the power head and including a vacuum line for connecting the hollow core of the sealing assembly to a vacuum source. The drum containment cabinet includes a lift for lifting the drum into sealing engagement with a first end of the sealing assembly to isolate a portion of the drum lid from the drum containment cabinet while exposing that portion of the drum lid to the filter/cutter assembly of the power head located in the power head chamber. The sealing assembly is closed when the powerhead is inserted therein. A vacuum pump is attached to the vacuum line of the sealing assembly for evacuating the vacuum chamber and a gas analyzer is connected to the vacuum line for analyzing gas drawn into the vacuum chamber created within the sealing assembly upon puncturing the drum with the filter/cutter assembly.

In still a further aspect of the invention, a computerized control system comprising a display subroutine, a control subroutine and a touch screen terminal is employed wherein the touch screen terminal displays a series of control commands for an operator to initiate by touching the screen of the terminal.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION

Figure 1:
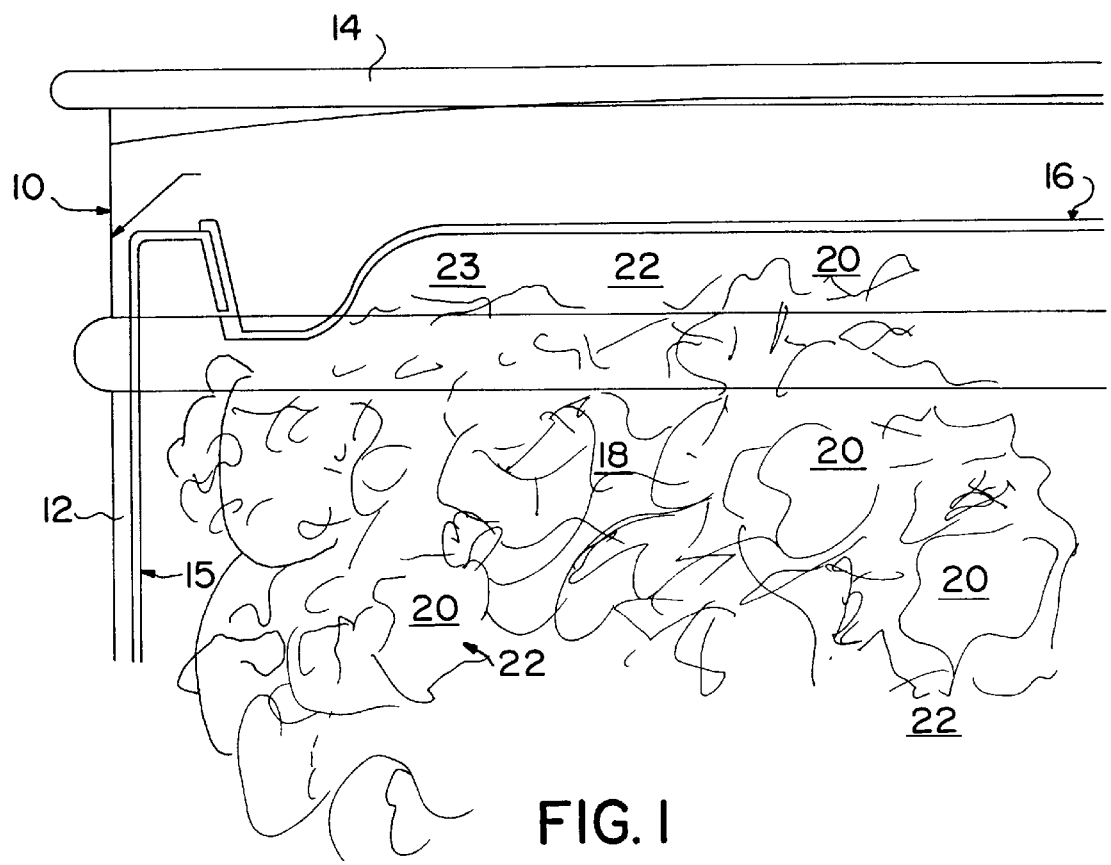
FIG. 1 is a side view, partially cut away showing a drum, the contents of which are to be tested and vented in accordance with the principles of the present invention.

The Drum Being Vented—FIG. 1

Referring now to FIG. 1, there is shown a top portion of a fifty-five gallon drum 10 which is comprised of a side wall 12, a drum lid 14, a high density polyethylene liner 15 and a liner lid 16. The drum 10 is filled with transuranic waste 18 having voids 20 therein in which headspace gases 22 accumulate. There is the possibility that the headspace gases 22 include hydrogen, methane or volatile organic compounds (VOCs) either generated by or contained within the voids 20 of the transuranic waste material 18. When headspace gases 22 are present, there is the possibility of the gases exploding and rupturing the liner lid 16 as well as dislodging the drum lid 14. The transuranic waste material 18 may be ejected by the explosion into the atmosphere or otherwise escape into the surrounding environment. Since the waste material is also radioactive, a hazardous situation then exists.

In view of the aforementioned considerations, it is necessary to test headspace gases 22 which may have accumulated in the voids 20 in the waste 18. The gases 22 are accessed via a headspace 23 a filtered vent to prevent accumulation of these gases in the drum 10, upon installing a confined area, which accumulations may lead to explosions releasing radioactive material. These requirements are in regulations set forth as waste acceptance criteria of the Department of Energy WIPP facility.

Figure 2:
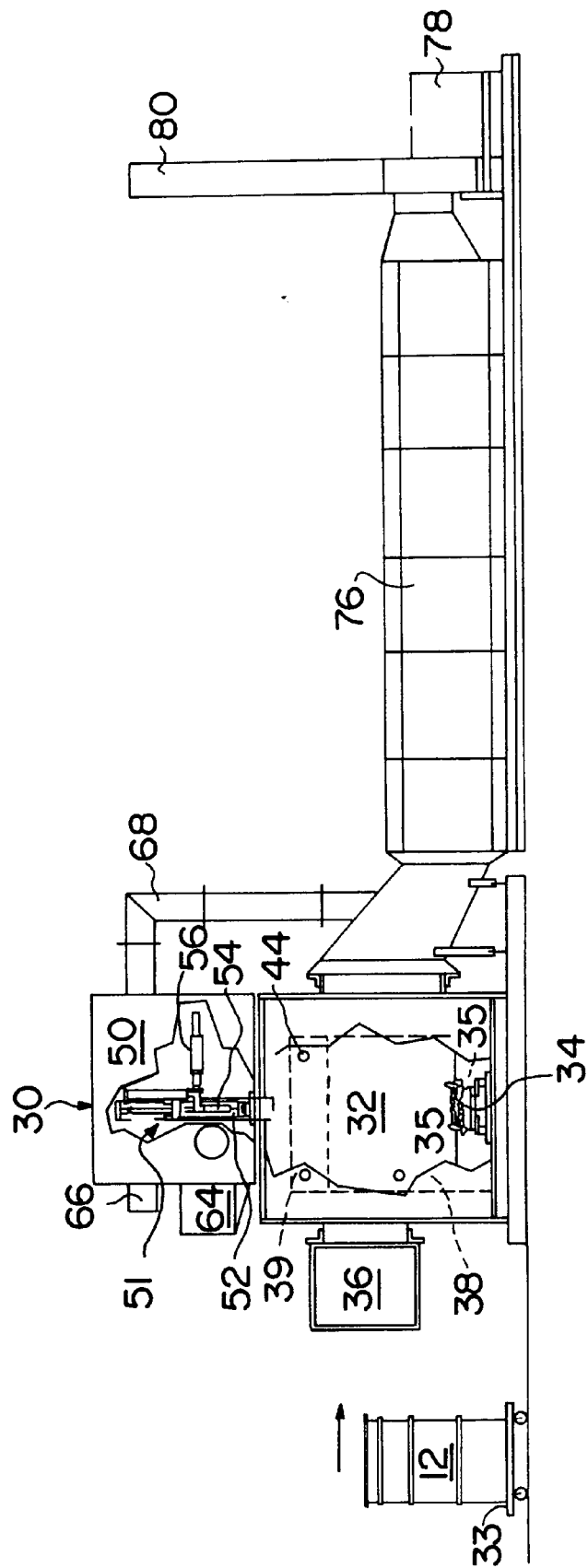
FIG. 2 is a side view of a drum testing and venting system in accordance with the present invention showing the drum inserted in the system but not raised.
Figure 3:
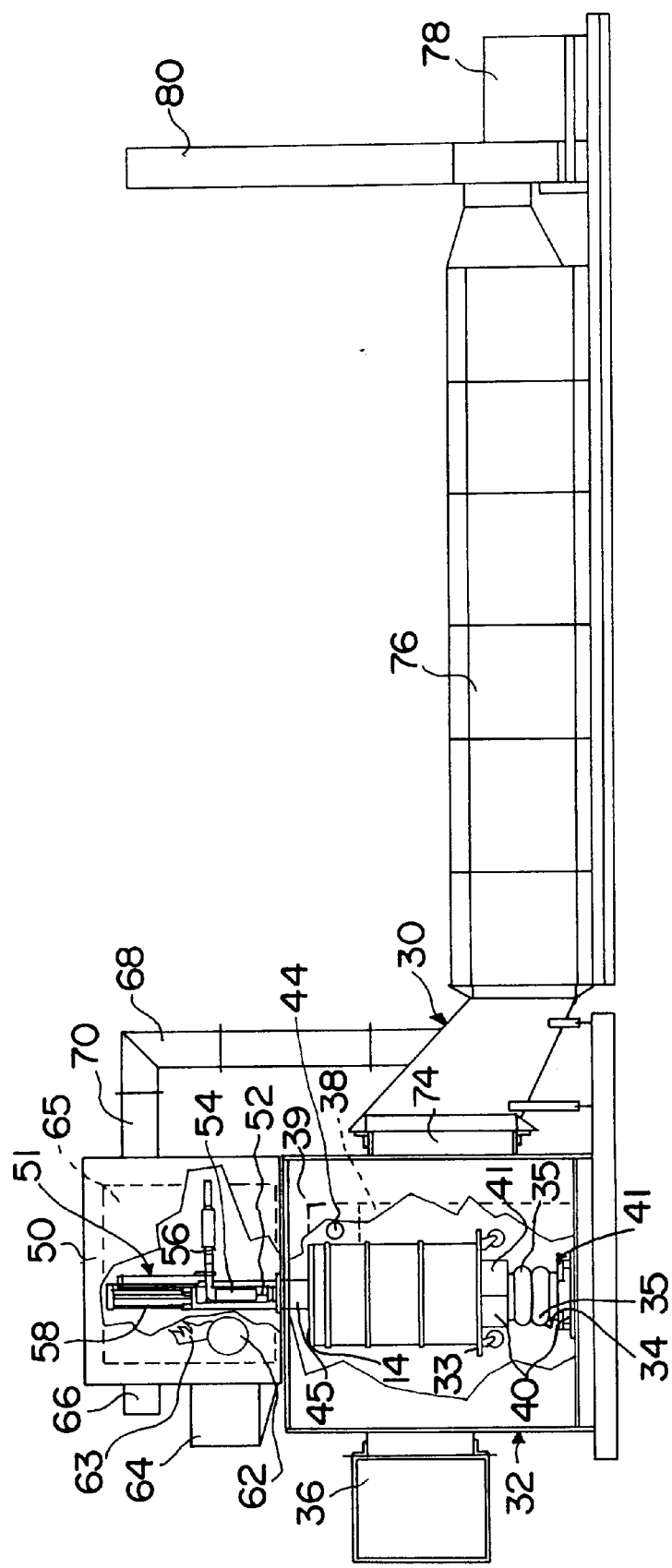
FIG. 3 is a view similar to FIG. 2 but showing the drum in a raised position in which a filtered vent is inserted and the gas contents thereof tested.

The System for Venting the Drum—FIGS. 2 & 3

Referring now to FIGS. 2 and 3, there is shown a drum venting system 30 comprising the apparatus of the present invention for practicing the method of the present invention. The drum venting system 30 includes a drum containment cabinet 32 in which the drum 12, while initially mounted on a wheeled dolly 33, is placed on a bellows-type drum lift 34 while either on or removed from the dolly so that the drum can be lifted from the FIG. 2 to the FIG. 3 position. The drum containment cabinet 32 is preferably a rectangular, heavy steel plate structure which can enclose either the fifty-five gallon drum 10 or an eighty-three gallon overpack drum (not shown). The cabinet 32 is of a sufficient size to dissipate pressure from a worst case scenario in which headspace gas 22 (FIG. 1) ignites, resulting in maximum drum pressurization of 136 psig and a maximum cabinet 323 pressure of over 15 psig. The cabinet 32 defines a first space for isolating the drum 10 from the adjacent environment.

Attached to the side of the drum containment cabinet 32 is a filter housing 36 which contains an HEPA (high efficiency particulate air) filter for inlet air drawn into the cabinet. The filter housing 36 includes backflow prevention device to minimize the risk of filter failure in case of overpressurization due to an explosion in the cabinet 32. The cabinet 32 preferably has a large access door shown in dotted lines at 38 and a small access door shown in dotted lines at 39. The small access door 39 is used to inspect the top surface of the drum lid 14 prior to lifting the drum 10 and after venting the drum. Both the door 38 and the door 39 are heavily gasketed to provide a seal during both normal operating conditions and abnormal events. Both the door 39 and the door 38 have sensors to tell the operator as to whether or not the doors are open or closed.

The pneumatic drum lift 34 also includes two force transducers 40 and 41 to provide downward force information. Following placement of the drum 10 on the drum lift 34, the drum is raised slightly until stopped by detection with a photosensor 44 in order to permit the force transducers 40 and 41 to weigh the drum. The drum 10 is then lifted to seal against a drum lid seal 45 by expanding the bellows of the pneumatic drum lift 34, as is seen in FIG. 3. By adding a predetermined sealing force (of about 200 pounds) to the total weight of the drum 10, a total upward force lift acquired to seal the drum is determined.

Disposed above the drum containment cabinet 32 is a glovebox 50. The glovebox 50 is in communication with the cabinet 32 through the drum lid seal 45. The glovebox 50 defines a second space which includes a power head 51 comprising a filter/cutter assembly 52 mounted in a socket sleeve 54 which is driven to rotate by a nutrunner 56. A screw-type linear drive 58 lowers the filter/cutter assembly 52 and socket sleeve 54 through the drum lid seal 45 so that it can penetrate both the drum lid 14 and the lid liner 16 of the drum 12 (see FIG. 1). A stepper motor (not shown) is mounted in the glovebox 50 for translating the linear drive 58 while the nutrunner 56 is driven by an integral DC motor.

The glovebox 50 includes a glove port 62 therein which has a glove 63 secured therein that extends into the glovebox so that the socket sleeve 54 may be manipulated to change filter cutter assemblies 52 or to insert new filter cutter assemblies for installation in a subsequent drum 10. An air lock 64 permits insertion of filter/cutters and other small components into the glovebox 50 as needed and window 65 is provided in the glovebox so that the operation may be observed and for facilitating manipulation of the various components with the glove 63.

An inlet air HEPA filter 66 is connected to the glovebox 50 and air is drawn into the glovebox 50 through the filter by low pressure created in a pipe 68. The pipe 68 has a damper/backflow preventer 70 therein and is connected to a transition duct 72 which in turn is connected to an outlet 74 of the drum containment cabinet 32. Accordingly, air is also drawn from the air inlet filter 36 through the drum containment cabinet and into the transition duct 72. The air then flows through a duct 76 as it is drawn by a blower motor 78 and is exhausted to the atmosphere through an exhaust stack 80. The duct 76 preferably includes a roughing filter and two high efficiency particulate air (HEPA) filter elements arranged in series so that radioactive particles are not discharged into the atmosphere.

Figure 4:
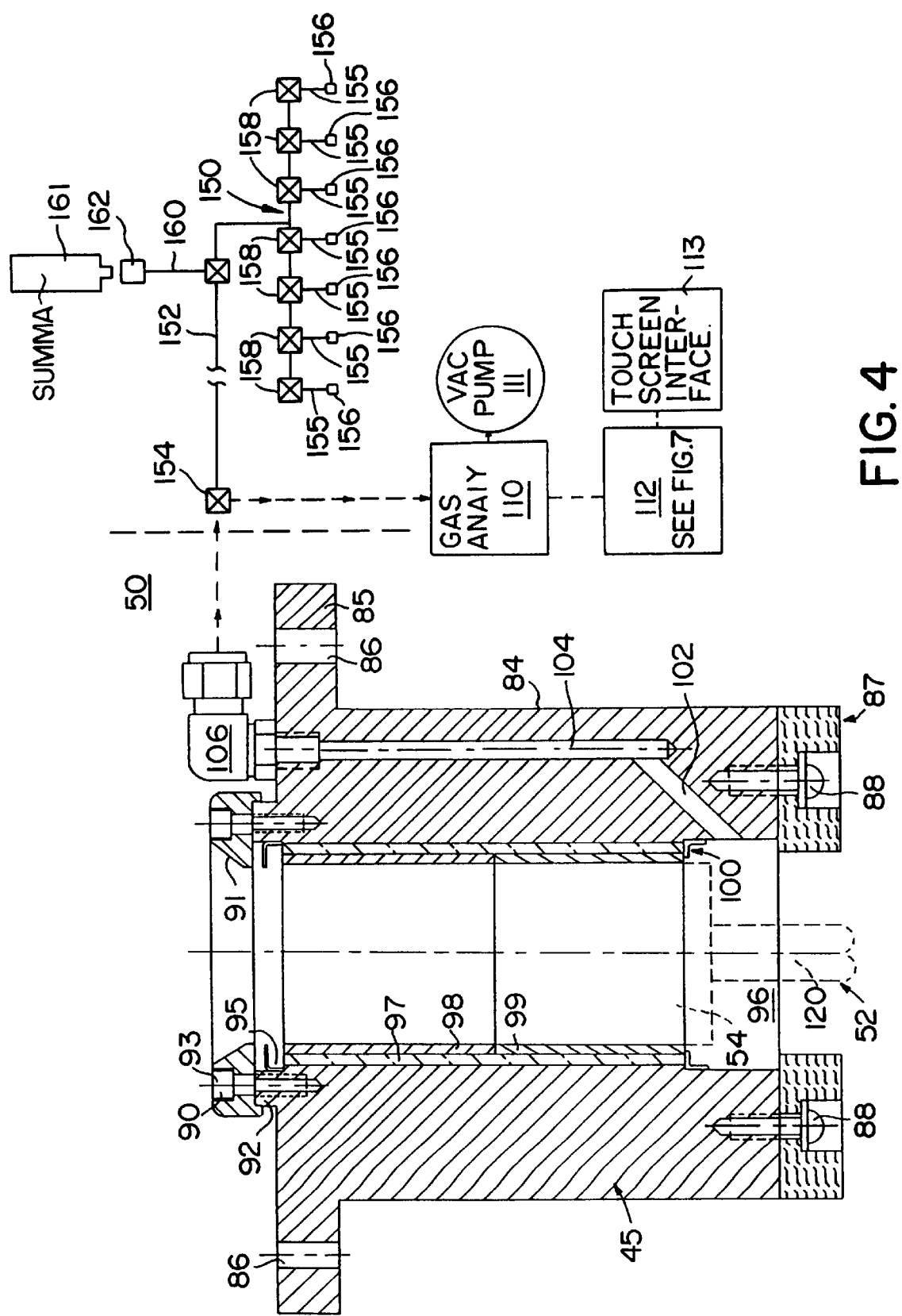
FIG. 4 is an enlarged side elevation of a seal used with the system of FIGS. 2 and 3 with a retaining sleeve and filter/cutter inserted therein shown in dotted lines.

The Seal—FIG. 4

Referring now to FIG. 4, wherein the annular seal 45 is shown in detail, it is seen that the seal is comprised of a seal housing 84 having a flange 85 with holes 86 therein for bolting to the floor of the glovebox 50. At its lower end, the housing 84 has an annular molded seal 87 which is secured to the housing 84 by bolts 88. The seal 87 seals against the top surface of the drum lid 14 and is made of a flexible material such as neoprene rubber. At the top of the housing there is socket centering ring 90 which has a chamfered inside diameter. The C-ring 90 is bolted to an annular collar 92 by a plurality of bolts 93. Just beneath the C-ring 90 is the upper annular seal 95. The housing 84 defines a hollow core 96 which is lined with cylindrical bronze bearing 97 that has disposed thereagainst an upper Rulon sleeve 98 and a lower Rulon sleeve 99. At the lower end of the Rulon sleeve 99 and the bronze bearing 97 there is a lower annular seal 100. The upper and lower annular seals 95 and 100 are Chicago-Rawhide #22328 seals which fit around the socket sleeve 54 of FIG. 3 to make the hollow core 96 of the housing 84 a substantially air tight chamber when the socket sleeve is inserted into the hollow core. The hollow core 96 defines a third space which is isolated from the first space defined in the interior of the cabinet 32 and is accessed via the second space defined by the interior of the glovebox 50.

Housing 84 has a pair of intersecting bores 102 and 104 therein. The first intersecting bore 102 is connected to the hollow core 96 of the housing 84 at one end at the other end to the second bore 104. The second bore 104 is coupled by an elbow joint 106 to a gas analysis system 110 which also includes a vacuum pump 111.

The gas analysis system 110 analyzes the headspace gases 22 which have accumulated in the headspace and voids 20 beneath the liner lid 16 and drum lid 14 of FIG. 1. A preferable system for the headspace gas analysis is a Varian Model 3800 gas chromatograph connected to a Varian SATURN 2000 Mars Spectrometer which system has been tuned and calibrated to identify and quantify hydrogen, methane and a selection of volatile organic compounds such as toluene, benzene, MEK, acetone or other organic compounds, some of which are more hazardous than others. Other systems, such as a Gas Chromatograph/Mars Spectrometer or Fourier Transform Infrared Spectrograph may be used for headspace gas analysis. The gas chromatograph utilizes a dual column system including a flame ionization detector to detect the volatile organic compounds and a thermal conductivity detector to detect hydrogen and methane. This system collects a real time sample of drum headspace gases 22 which has accumulated in the voids 20 and within about 5 minutes completes the analysis and prints out the gas concentration results. The gas chromatograph 110 is connected to a PC 112 which automates the analysis and quantification of headspace gas results and energizes an alarm 114 if combustible gas concentration exceeds established safety levels.

Figure 5:
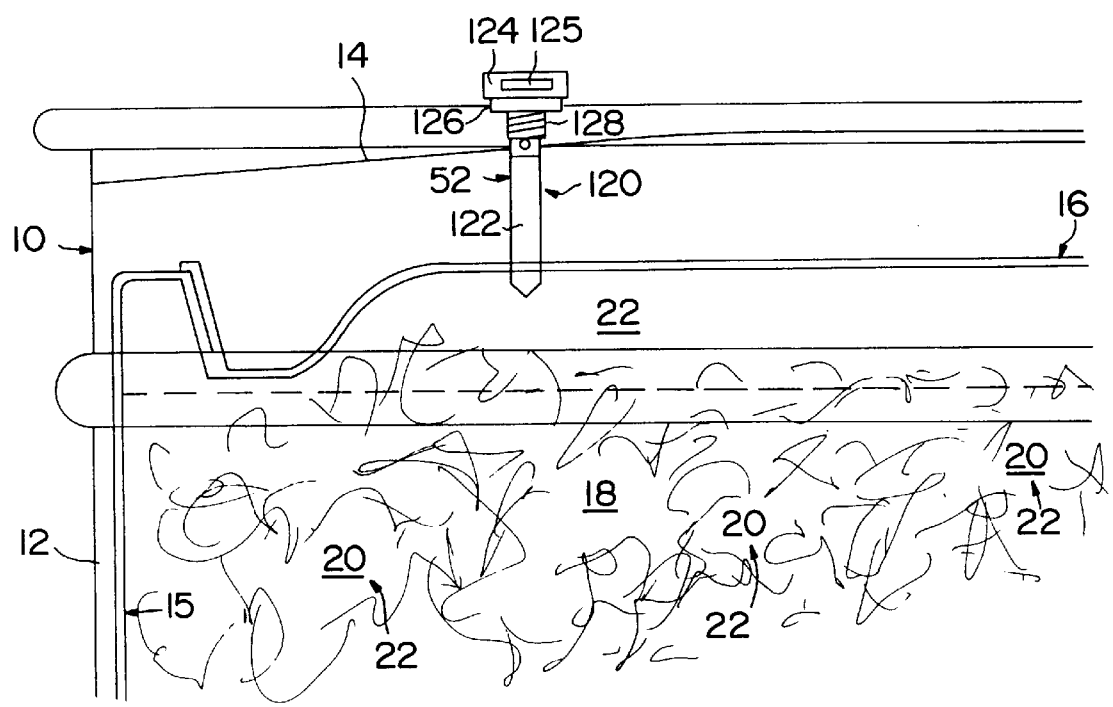
FIG. 5 is an enlarged side view of a top portion of the drum with portions cut away showing a vent, with an integral filter, inserted through the drum lid and liner lid of the drum but not seated.
Figure 6:
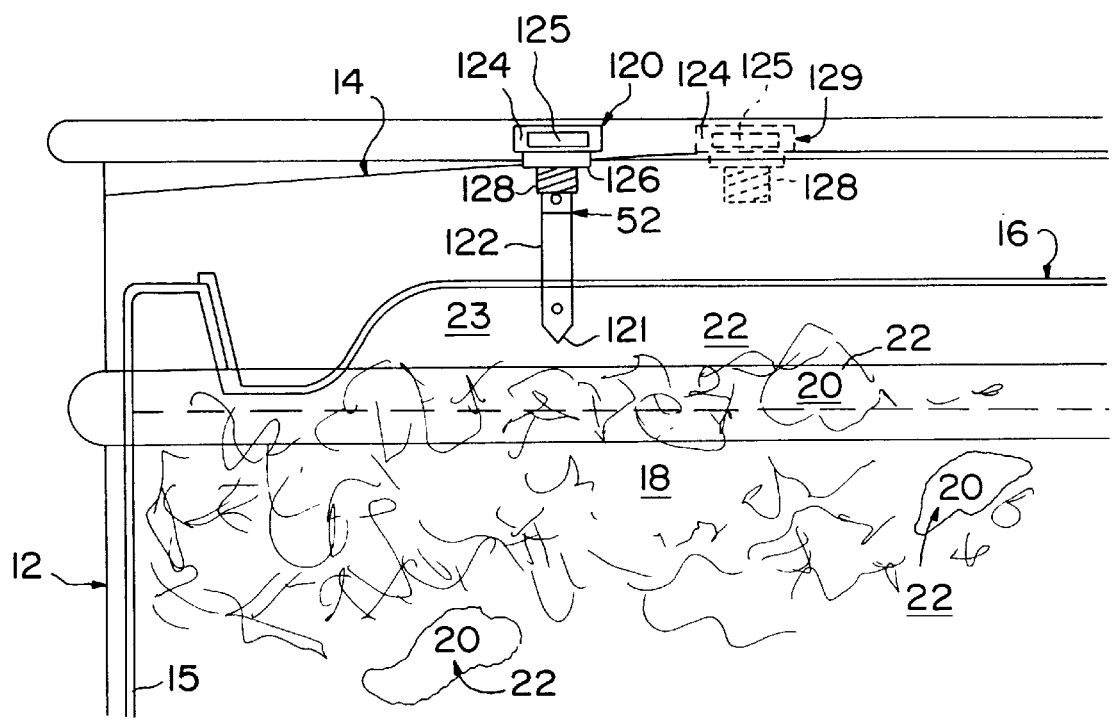
FIG. 6 is a view similar to FIG. 5 but showing the vent threadably secured in the drum lid.

Installation of the Vent—FIGS. 5 & 6

Referring now to FIGS. 5 and 6, there is shown a filter/cutter vent 120 to be installed in accordance with the principles of the present invention wherein the filter/cutter vent 120 includes a drill point 121 or a projecting stem portion 122 which penetrates the drum lid 14 and the liner lid 16 to reach the interior of the drum 10 in which the headspace gases 22 have accumulated from transuranic waste material 18 stored within the drum headspace 10. The filter/cutter vent 120 has a head portion 124 which includes a HEPA carbon filter element 125 for preventing the discharge of particulates into the hollow core 96 of the sealing sleeve 45. The filter/cutter 120 assembly further includes a sealing gasket 126 which seals around the opening through the drum lid 14 and self-tapping helical threads 128.

During installation, the filter/cutter 120 is initially rotated at a relatively high speed so that the drill point 121 cut through the drum lid 14 and thereafter is rotated at a relatively slow speed so that the self-tapping threads 128 tap into the drum lid in order to retain the filter/cutter 120 in place to vent the drum 10.

There are two versions of the filter, i.e., a long stem version 120 and a short stem version 129 (shown in dotted lines). The short stem version is used if it has been found that a long stem version hits an impenetrable mass or object protruding from the transuranic waste material 18. When it has been found that the filter cutter 120 will not advance because an impenetrable object has been encountered, then the socket sleeve 54 is raised and the operator changes the filter/cutter assembly 120 to a short stem version 129.

Preferably, the cutting end or drill-type tip 121 of the tubular portion 122 is made of hardened tool steel with the housing portions of the units made of 316 stainless steel. The filter media 125 within the head 124 is a carbon-bonded-carbon material performance tested to provide greater than 99.97% removal of $0.3\,\mu$ to $0.7\,\mu$ particles. The air delivery capacity of the filter is 200 ml/min at 1 inch of water column change in pressure.

There are drums 10 which have been previously vented and equipped with filters, such as the filter/cutter vent 120, or any other type of vent or combination filter vent and therefore do not need a filter/cutter vent installed. These drums do not need to be placed in the cabinet 32 and sampled through the glovebox 50. In order to provide the system 30 of FIG. 2 with the capability of sampling such drums, an exterior manifold 150 is connected by a flexible line 152 to the gas analyzer 110 by a valve 154 (see FIG. 4). The exterior manifold 150 is positioned outside of the glovebox 50 and has lines 155 with drum seal cups 156 which are placed over vents preexisting in the drums 10. Each line 155 has a valve 158 which valves are preferably operated in sequence by a computerized control system, such as that of FIG. 7, which opens the valves sequentially and evacuates the gas analysis system 110 with the pump 111 after each drum 10 has been sampled. The computer control system also initially opens valve 154 to select the exterior manifold 150 rather than the drum lid seal 45 in the glovebox 50. The exterior manifold 150 also includes a connection 160 for coupling with a SUMMA canister 161 via a valve 162, a SUMMA canister being a canister containing a gas sample from a remote location.

Figure 7:
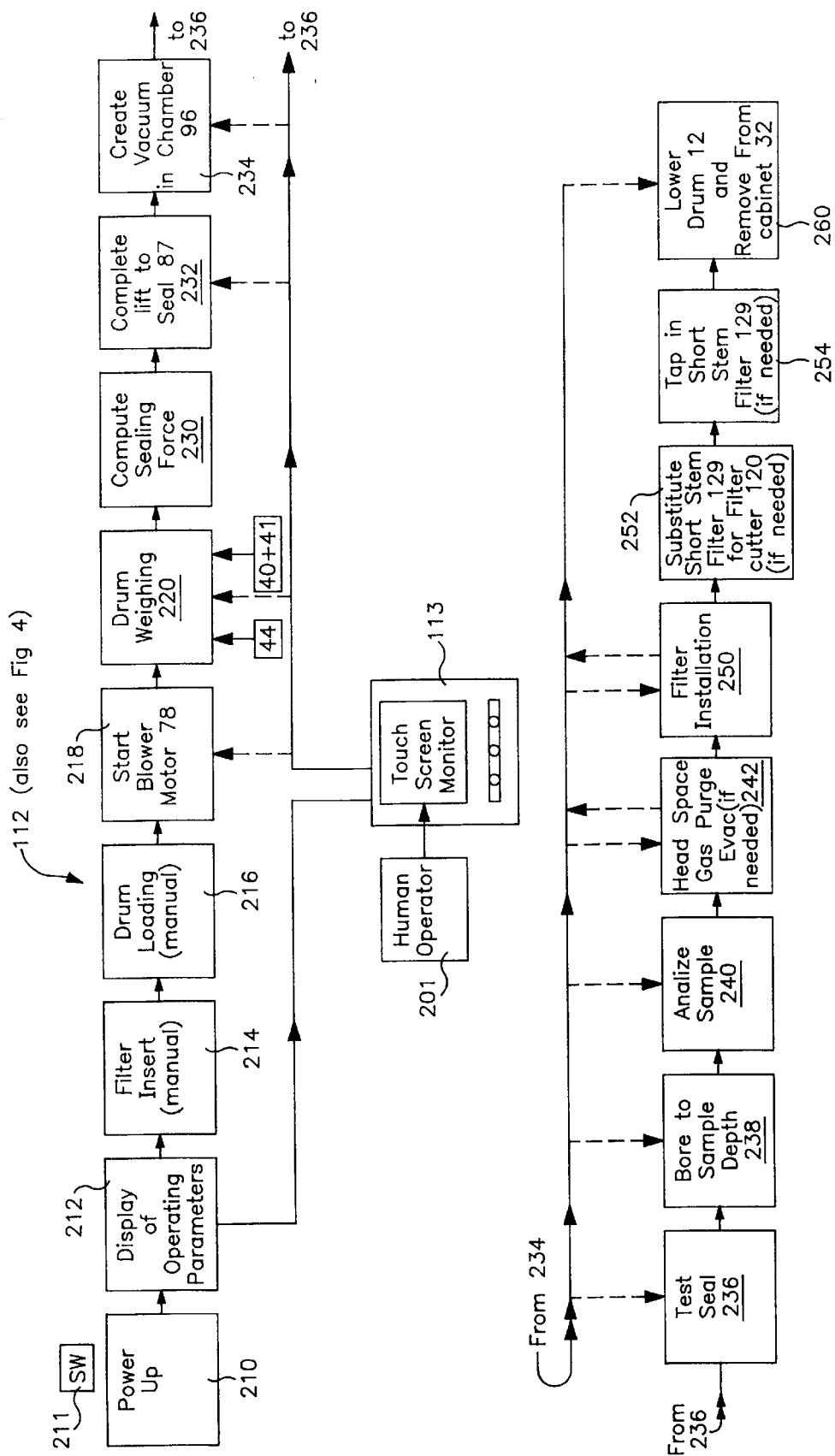
FIG. 7 is a diagrammatical view showing the operational steps comprising the method of practicing the present invention.

The Metdhod Steps—FIG. 7

Referring now to FIG. 7, in order to control the system shown in FIGS. 2 and 3 and the components thereof illustrated in FIGS. 1, 4, 5 and 6, the industrial process controller 112 (see FIG. 4) interfaces between the system 30 and its qualified human operator 201. As is seen in FIG. 7, the industrial process controller 112 is connected to the touch screen interface 113 which allows the operator to control the drum venting process.

Initially, the system is turned on in a power-up step 210 in which the drum venting system 30 is provided with 125 VAC power and the air handling train is provided with three phase 240 VAC power. The power step is accomplished by throwing switches 211.

In the next step, the current operating parameters are displayed on the touch screen interface 113 controlled by a display controller 212, which operating parameters can be adjusted by the human operator 201. A filter insert step 214 is then performed in which the filter cutter 120 of FIG. 5 is manually inserted in the socket sleeve 54 of FIG. 3 by using the glove 63 of the glovebox 50.

Initially, the drum lift 34 is in the FIG. 2 position and the drum loading step 216 is accomplished by opening the door 39 of the drum cabinet 32 and placing a bridge platform in the opening so that the drum 12 and dolly 33 are loaded into the drum cabinet 32 in a way to prevent the door from closing prematurely. The bridge platform is then removed and the door 39 to the drum containment cabinet 32 is closed. This completes the manual phase of the operation.

The automatic phase begins in step 218 where the blower motor 78 is started and brought up to speed in order to create a negative pressure in the cabinet 32 with respect to the drum 10. After starting the blower 78, the drum weighing step 220 is initiated wherein pressurized air flows into the doughnuts 35 of the drum lift 34 which raises the drum 10 to a detection level (FIGS. 3 and 4) where a photoelectric sensor 44 senses that the drum has now been elevated and the lift 34 halts raising the drum so that transducers 40 and 41 can compute the weight of the drum.

In step 230, the sealing force with which the drum 10 must be pressed against the annular rubber seal 87 of the sealing sleeve 45 is computed by adding the sealing force to the weight of the drum. This is necessary because there is a variation in the weights of various drums 12 depending on the transuranic waste material 18 within the drums.

In step 232, the drum 10 is pressed against the annular seal 87 with the requisite force as again measured by the transducers 40 and 41. Upon the transducers 40 and 41 sensing the appropriate lift force to seal the drum against the annular seal 87 of the sealing sleeve 45, the operator 201 initiates a signal which causes the socket 54 of the drill assembly power head 51 to lower into the hollow core 96 of the sealing sleeve 45 (see FIG. 4). As the socket 54 lowers into the hollow core 96, a vacuum is applied in step 234 to first and second bores 102 and 104 of the sleeve 45 by vacuum pump 111 to create a vacuum in the hollow core 96 sealing sleeve 45 (see FIG. 4).

It is important that the hollow core 96 of the sealing sleeve 45 maintain its vacuum. The pressure within the hollow core 96 is then monitored in a seal test step 236 over a short period of time. if there is a rise in pressure within the hollow core 96, the operator may elect to reform the vacuum by again applying a vacuum to the hollow core or by backing out the sleeve 54 and lowering the drum from engagement with the annular seal 87 and then repeating steps 32–36. The operator may also decide to proceed with the test, noting that the headspace gas analysis results may be compromised by outside air.

The next step is the boring step 238, wherein the nutrunner 56 is rotated at boring speed and descends on the linear drive 58 so that the drill point 121 bore through the drum lid 14 and the liner lid 16. Once the liner lid 16 is penetrated, rotation of the filter/cutter 120 ceases and headspace gas fills the vacuum chamber created in the hollow core 96 of the sleeve 45 by gas flowing through the filter 125 in the head 124 of the filter cutter. The headspace gas then flows, or is rather drawn, by the gas chromatograph in the analyzing system 110 through the first bore 102 and second bore 104 (see FIG. 4) for analysis in an analysis step 240. Upon completion of the gas analysis, the GC Personal Computer 112 displays the results.

If there is an undesirable concentration (greater than LEC) of combustible gas such as a volatile organic compound, hydrogen or methane, the operator 201 initiates an evacuation/purge cycle step 242 in which a vacuum is applied to the bores 102 and 104 through the fitting 106 to partially evacuate the gas in the headspace 22. After a partial evacuation, nitrogen is pumped through the bores 102 and 104 until the amount of combustible gas sensed is at a safe level.

After the headspace gas is purged (if necessary), the filter installation step 250 is performed wherein the controller for the nutrunner 56 and the linear drive 58 (FIG. 3) operate at a feed rate and rotational speed matched to the thread pitch 128. Rotary and downward motion continues until the torque transducer output of the nutrunner 56 achieves a predetermined setting of 12 to 18 foot pounds which indicates that the filter cutter 120 is properly installed and seated with the gasket 126 sealing against the drum lid 14 (FIG. 6).

During either installation of the filter in step 250 or boring to the sample depth in step 238, an impenetrable object is encountered preventing descent of the filter/cutter 120, the nutrunner 56 and linear drive 58 cease operation and the operator is alerted by an indication on the touch-screen monitor 113. The operator 201 then directs the power head assembly 51 to retract the filter/cutter 120 into the glovebox 50, wherein in step 252 the long stem filter/cutter 120 is replaced manually with the short stem filter 129. In almost all cases, the long stem filter/cutter 120 will have cut through the liner lid 16 (FIGS. 1, 4 and 5) so that the space 22 is open to the space between the drum lid 14 and liner lid 16. Accordingly, the short stem filter 129 need only be long enough to self tap into the drum lid 14 in step 254.

After the filter/cutter 120 is installed, the drum 10 is lowered and unloaded from the drum cabinet 32 in a final step 260. When the drum 12 is lowered, the small access door 39 to the cabinet 32 is opened so that the drum lid 14 can be checked for radioactive contamination. If contamination is found, the drum lid 14 is wiped clean before removing the drum 12 from the cabinet on its dolly 41. A subsequent drum 10 is then installed following steps 214 through 260, unless the system is to be shut down in which case the subsequent drum is tested starting with step 210.

Software Description and Integration

In a preferred embodiment, Project Logic Control software is employed to operate and automate all functions of the drum venting system 30. Exemplary of software used is that produced by Omrom Inc. of Shawnburg, Ill., and is referred to as Ladder Support Software Version 3 (LSSv.3) incorporated herein by reference. The final release version of this software has the control number DVSLSS 110 incorporated herein by reference.

The software consists of a main program in twenty-six separate and distinct sub-routines. The main program contains ladder logic instructions that call on each of the twenty-six sub-routines and the sub-routines are of two types. The first type of sub-routine is responsible for performing specific physical actions or tasks with respect to the drum 10 and the second type of sub-routine displays the result of the specific action or task identified in the subroutine by screen numbers. In the preferred embodiment, the Project Logic Control utilizes a touch screen programmable terminal 202 to interface with the operator.

EXAMPLE

A detailed example as to how an embodiment of this invention is practiced is set forth in the following four sections:

I) a detailed sub-routine and processing description,

II) a linear drive hexadecimal to binary conversion table,

III) switch condition sub-routines, and

IV) sub-routine and screen bit cross-reference tables.

I. DETAILED SUBROUTINE & PROCESSING DESCRIPTION FOR THE TRANSURANIC (TRU) DRUM VENTING SYSTEM (DVS)

TRU DVS Software Subroutines: The following is a list of all TRU DVS steps/subroutines used by the TRU DVS PLC software in the control of the drum venting process:

00. MANUAL POWER UP (MANUAL OPERATION)

Note, in reality this is not a true software subroutine, but an essential step in the process. The operator(s) unlock the Electrical Equipment Enclosure and switch the main circuit breaker to the ON position. Operator(s) must verify that all branch circuit breakers in the electrical equipment enclosure cabinet are in the ON position. Operator(s) clean the lid of the drum to be processed and place drum on the trolley.

The PLC is placed in monitor mode by appropriately setting Data Memory location DN 6600 such that on POWER-UP screen #1, INTRODUCTION, is displayed. The display of screen #1 at POWER-UP is designated as path 1 on the flowchart.

The HEPA blower motor will also turn on and rotate at a software "hardwired" high speed. For example, when the DVS is initially electrified, the HEPA blower motor will rotate at 73 to 75 RPM which insures an adequate air flow into, and through, DVS cabinet and glovebox when either the cabinet door and/or glovebox door is open. When both doors are closed, the motor is commanded to rotate at a slower speed which is set by the operator in the CHANGE subroutine.

0. STARTUP

This is the first of the subroutines and its designation is subroutine number 000 in the DVS ladder logic software. STARTUP displays screen #1, INTRODUCTION, for 15 seconds. This screen introduces the operator to the NFT DVS product.

After 15 seconds screen #3, START MODE, is displayed. This change of system state is denoted as path 2 of the flowchart. Screen #3 displays a BEGIN touch switch. The DVS process will not proceed until BEGIN is pressed. When BEGIN is pressed screen #4, WARM-UP, will be displayed. WARM-UP displays for 120 seconds. A minutes and seconds count-down clock is displayed so the operator is made aware of the time remaining in the WARM-UP period. During the warm-up period all bits in internal register (IR) and Data Memory (DM) that require initialization are initialized.

1. CHANGE

When the warm-up period has terminated, screen #5, DISPLAY PARAMETERS, is displayed. This change of system state is denoted as path 4 on the flowchart. This is the second subroutine and is designated as subroutine number 001. CHANGE displays screen #5 which enables the operator to view the present setting of the following operator presettable parameters:

1. Seal Force.
  2. Seal Test Evac Pressure
  3. Drum Evac Pressure
  4. Drum Purge Pressure
  5. HEPA Blower Motor Speed
  6. Linear Drive Load Cell Zero Adjustment.

Screen #5 also displays a NEXT touch switch. Pressing NEXT causes screen #80, CHANGE PARAMETERS, to be displayed. This is path 5 on the flowchart.

Screen #5 displays three touch switches; YES, NO, and REVIEW. If the operator needs to look at the parameters settings again, pressing REVIEW will causes screen #5, DISPLAY PARAMETERS, to again be displayed. Flowchart path 6 will be traversed when REVIEW is pressed. Pressing NO will cause execution to switch to subroutine 002, INSERT FILTER, and screen #24, INSERT STANDARD FILTER, will be displayed. This corresponds to path 7 of the flowchart. Finally, pressing YES causes screen #81, ENTER PASSNUMBER, to be displayed. This is path 8 of the flowchart.

, with YES and NO touch switches, whether or not to change the following process parameters:

1. Seal Force—the upward force exerted on the drum lid by the seal on the bottom of the quad seal housing. Force in pounds units.
  2. Seal Test Evac Pressure—the negative air pressure limit within the chamber formed by the cylindrical walls of the quad seal housing, the drum lid, and the bottom of the socket during the seal test. Pressure in PSIA.
  3. Drum Evac Pressure—the negative air pressure limit within the drum during an evacuation cycle. Pressure in PSIA.
  4. Drum Purge Pressure--the positive air pressure limit within the drum during a purge cycle. Pressure in PSIA.
  5. Blower Motor Speed—the speed of the HEPA Blower motor in RPM. The blower motor speed should never exceed 80 RPM.
  6. Linear Drive Force Load Cell Zero Adjustment—this is not a parameter per se. The DVS software permits the operator to adjust the upward tension on the linear drive load cell or strain gage so that its output may be zeroed when no force is being applied to the linear drive assembly.

If YES is pressed, CHANGE will display screen #5 which queries the operator as to whether or not it is Seal Test Pressure that is to be changed. YES and NO touch switches are displayed. If YES is pressed, the operator is presented with screen #6 which depicts a keyboard that enables operator to change the seal evac test pressure setpoint. If NO is pressed, execution leaves the CHANGE subroutine (001) and switches to the INSERT FILTER subroutine (002). The operator is presented with screen #24 of the INSERT FILTER subroutine.

2. INSERT FILTER (MANUAL OPERATION)

This subroutine is designated as 002. Screen #24 instructs the operator to insert a standard filter into the recess of the socket and press the READY touch switch when the operation has been completed. Pressing the READY touch switch causes execution to switch to the LOAD DRUM subroutine (003).

3. LOAD DRUM (MANUAL/IPC OPERATION)

This subroutine is designated as 003. Screen #25 instructs the operator to the drum into the cabinet a press the READY touch switch when the operation has been completed. If there is a drum in the cabinet and the cabinet and access doors are closed, pressing the READY touch switch will cause execution to switch to the NITIALIZATION subroutine (004).

ERROR CONDITIONS

A. The cabinet door is open or ajar
B. The access door is open or ajar
C. A drum has not been enclosed in the cabinet If any one of the above error conditions is true, screen #26, LOAD DRUM ERRORS, will be displayed. This screen uses lamps to indicate to the operator which of load drum enable conditions has not been satisfied. After 15 seconds, screen #25, LOAD DRUM, is again displayed. The operator, after noting the error condition(s) from screen #26, may then correct the error condition(s), press READY, and proceed to the next subroutine. Otherwise, screen #26, LOAD DRUM ERRORS, will appear each time the READY touch switch of screen #25 is pressed and an error condition exists.

4. INITIALIZATION IN PROGRESS

This subroutine has ladder logic designation number 004. The INITIALIZATION commands the DVS, HEPA filter-train, blower-motor speed controller to turn the motor ON and operate it at a speed controlled by a ladder logic setpoint. Presently, the motor speed setpoint is 43.2 Hz. Screen #27, IN PROGRESS, is displayed for 15 seconds, giving the motor time to come up to speed.

5. INITIALIZATION DONE

After 15 seconds, execution will switch to subroutine 005 and screen #28, SYSTEM INITIALIZED, will be displayed. In other words, the blower-motor has achieved the setpoint RPM rotation velocity. An ENTER touch switch is displayed on screen #28. Pressing ENTER will cause execution to switch to the subroutine 006.

6. WEIGH DRUM 1

Ladder logic subroutine 006 simply displays screen #29, WEIGH DRUM. This screen informs the operator that pressing the touch switch labelled WEIGH will initiate the weigh drum step of the process.

7. WEIGH DRUM 2

When WEIGH is pressed, execution switches to subroutine 007 and screen #30, IN PROGRESS, is displayed. While screen #30 is visible, the PLC of the DVS opens valves enabling pressure regulated air to inflate an airbag actuator. The inflating airbag extends vertically upward until it makes contact with the bottom of the dolly on which the drum rests. Both the dolly and the drum are lifted upward until a photosensor beam, positioned approximately one inch above the rim of the unlevitated drum, is broken by the rim of the raised drum. The broken beam signals the PLC that the dolly/drum assembly is fully levitated.

8. WEIGH DRUM 3

In response to the broken photosensor beam condition, execution is switches to subroutine number 008 and screen #31, DRUM WEIGHED, is displayed. Furthermore, the PLC configures the DVS solenoid valves to retain air in the airbag actuator or lift. As a result, the dolly/drum assembly remains at a specific height above the cabinet floor. Screen #31 displays the weight of the 55 gallon drum and its contents. When touch switch, RAISE, is pressed, execution switches to subroutine 009.

ERROR CONDITIONS

A. The DVS software will no longer detect a drum over-weight condition.

B. Drum weight step timer expired or timed-out.

If condition B. is true, screen #33, WEIGH DRUM TIME-OUT, is displayed. Screen #33 displays two touch switches: RETRY and ABORT. If RETRY is pressed, execution is switched to subroutine 006, and the weigh drum step is repeated. If ABORT is pressed, execution switches to subroutine #027, LOWER DRUM. LOWER DRUM will configure the DVS solenoid valves such that air expelled from the air actuator, ensuring the descent of a partially raised drum/dolly assembly.

9. RAISE DRUM 1

Subroutine 009, RAISE DRUM 1, configures the valves of the DVS such that air is permitted to inflate the air actuator and raise the drum until its lid contacts the quadseal housing seal. As the drum is raised, screen #34, RAISE DRUM TO SEAL, is displayed. As the drum is raised, the topmost photosensor, photosensor #2, beam is interrupted by the drum. The DVS solenoid valves will remain in the "inflate air actuator configuration" until the drum lid makes contact with the quadseal housing seal with a force that is equal to, or greater than, the seal force setpoint parameter AND the OFF condition of photosensor #2. When these conditions are true, the DVS PLC configures the solenoid valves to retain air in the air actuator such that the drum lid remains firmly pressed against the quadseal housing seal. Furthermore, execution will switch to subroutine 010.

10. RAISE DRUM 2

Subroutine 010, RAISE DRUM 2, displays screen #35, DRUM RAISED. Screen #35 displays the present value (PV) seal force in pound units and the LOWER POWERHEAD touch switch. Pressing LOWER POWERHEAD causes execution to switch to subroutine 011, LOWER PH1.

11. LOWER PH1

Once LOWER POWERHEAD is pressed, the DVS PLC causes the linear drive controller to execute a series of preprogrammed linear motion sequences that lower the linear drive from its fully raised, or HOME position, until the tip of the filter is in contact with the drum lid. While the powerhead is descending, screen #37, LOWER POWERHEAD IN PROGRESS, is displayed. When the final linear motion sequence has terminated AND a certain minimum upward force is exerted upon the powerhead assembly via the contact force of the filter tip and drum lid, screen #38 is displayed. Furthermore, execution switches to subroutine 012, LOWER PH 2.

12. LOWER PH 2

Subroutine 012, LOWER PH 2, displays screen #38, POWERHEAD LOWERED, if the linear drive controller responded within a predetermined time AND the filter is touching the drum lid with a force greater than a predetermined minimum force AND an impenetrable object has not been detected during the boring or installation subroutine steps. Screen #38 depicts a SEAL/VAC touch switch that, when pressed, causes execution to switch to the SEAL TEST 1 subroutine, subroutine 013.

Subroutine 012, LOWER PH 2, displays screen #80, LOWER STUB FILTER FOR INSTALLATION, if an impenetrable object was detected during execution of the boring-to-sample depth subroutine, BORE 1, or execution of the installation subroutine, INSTALL 1. Screen #80 instructs the operator to remove the standard filter and replace same with a shorter, stub filter, such that installation may be effected regardless of the impenetrable object. Screen #80 also depicts an INSTALL STUB touch switch. Pressing INSTALL STUB causes execution to switch to the INSTALL 1 subroutine, subroutine 022.

ERROR CONDITIONS

A. The linear drive does not respond to DVS PLC commands to initiate linear movements. B. The linear drive has descended yet the touch-force on the filter tip is below the predetermined minimum, ie. there is no filter in the socket. Error condition A., the linear drive has not responded in a given period of time to PLC commands to initiate linear movements will cause screen #76, POWERHEAD MOVE TIME-OUT, is displayed. Screen #76 depicts an ABORT touch switch. When pressed, ABORT causes execution to switch to subroutine 027, LOWER DRUM 1 so that the drum may be lowered to the cabinet floor and the process terminated.

Error condition B., if there is no filter in the socket screen #39, NO FILTER IN SOCKET, is displayed. Screen #39 depicts a RETRACT touch switch. Pressing RETRACT causes execution to switch to the subroutine 024, RETRACT PH1. RETRACT PH1 must have appropriate screen to allow operator to insert standard filter and repeat LOWER PH1.

13. SEAL TEST 1

Subroutine 013, SEAL TEST 1, displays screen #40, SEAL TEST IN PROGRESS, for 90 seconds. Screen #40 displays an elapsed time, in seconds, count-down numerical display. The purpose of the seal test is to test the integrity or quality of the seal at the drum lid/quad seal housing seal interface and the socket/quad seal housing seals interface.

Implementation of the seal test is accomplished when the PLC turns ON the DVS vacuum pump AND activates, switches ON or OPENS solenoid valve, V3, allowing the vacuum pump to partially evacuate the air contained in the cylindrical chamber formed by the drum lid, the cylindrical walls of the quad seal housing, and the bottom of the socket. The vacuum pump will remain ON for 30 seconds. After 30 seconds, solenoid valve V3 will be deactivated, switched OFF or CLOSED and the vacuum pump switched OFF.

The pressure within the chamber is monitored by compound pressure transmitter, P1. The DVS seal assemblies are contrived to maintain a certain partial vacuum for a given period of time. The seal test is intended to measure the degradation of the partial vacuum in the chamber 60 second after its has been isolated from the ambient atmosphere by the closing of valve V3. In any event, after 90 seconds, the test is terminated and execution is switched to subroutine 014, SEAL TEST 2.

14. SEAL TEST 2

Subroutine 014 displays the results of the seal test. If the pressure in the chamber remains below an operator presettable setpoint value after 60 seconds, the seals are deemed to be "good." If the seals are good, screen #41 is displayed, SEAL TEST PASSED. Screen #041 depicts a BORE touch switch and a numerical display of the pressure within the chamber. Pressing BORE will cause screen #41 to disappear from view and screen #44 to be displayed instead. Screen #44 reminds the operator that relevant drum data is to be noted and logged. Screen #44 depicts a BORE touch switch. Pressing BORE causes execution to be switched to subroutine 015, BORE 1.

ERROR CONDITIONS

A. The seal test failed because the seals were inadequate and the pressure within the chamber could not be maintained below the operator presettable minimum.

If the pressure in the chamber rises above the operator presettable setpoint value after 60 seconds, the seals are deemed to be inadequate. If the seals are inadequate, screen #042 is displayed, SEAL TEST FAILED. Screen #042 depicts a BORE touch switch and a numerical display of the pressure within the chamber. Screen #042 instructs the operator to proceed with the BORE, SAMPLE, and FILTER INSTALLATION steps of the process even though adequate chamber seals could not be achieved. It is imperative that the operator note the seal test failure so that the sample/analysis results will understood to be compromised. Pressing BORE will cause screen #042 to disappear, and execution to switch to subroutine 015, BORE 1.

15. BORE 1

Subroutine 015 displays screen #45, BORE TO SAMPLE DEPTH IN PROGRESS, for 90 seconds. Screen #45 displays an elapsed time, minutes and seconds, count-down numerical display. While screen #45 is displayed, the DVS PLC activates the linear drive controller to execute six, consecutive, 0.040 inch linear motion sequence movements in which each of the six sequences terminates after 15 seconds. Simultaneously, the DVS PLC commands the nutrunner or rotary motion controller to execute six, consecutive, 200 RPM, high torque rotary sequences, each having a duration of 15 seconds. The combined result of the above is to cause the drill tip of the filter tip to drill and penetrate the TRU waste drum lid in 90 seconds.

After the sixth linear and rotary motion sequence has been executed to completion, the DVS PLC commands the linear drive to descend approximately 1.5 inches into the drum lid. The descent takes place in 30 seconds. The nutrunner controller is commanded to rotate the socket at 200 RPM during the two stage descent so that the 90 mil thick HDPE plastic liner will certainly be perforated. When the second linear motion sequence has been executed to completion, the DVS PLC switches execution to subroutine 016, BORE 2. Alternatively, an obstruction in the path of the descending filter tip will cause the DVS PLC to switch execution to subroutine 016, BORE 2.

16. BORE 2

Subroutine 016 displays screen #46 if an impenetrable object was not enncountered and all motion sequences executed to completion. Screen #46 informs the operator that sample depth (within the drum) has been achieved. The screen also displays a SAMPLE touch switch. When pressed, SAMPLE, causes execution to switch to subroutine 017 and the drum head space gases are sampled and analyzed by the DVS gas chromatograph.

ERROR CONDITIONS

A. An impenetrable object was in the path of the descending filter tip. If, during the execution of any of the above linear motion sequences, an impenetrable obstruction was in the path of the descending filter tip, the force on the linear drive assembly will quickly exceed factory preset limits and a "FAULT" condition occurs. The linear drive controller's FAULT output signal, input to the DVS PLC at discrete address 00103, will become TRUE. Thus notified, the DVS PLC will display screen #47, command the linear drive be retracted to the HOME or fully raised position, and set the "impenetrable object" bit.

When the powerhead or linear drive assembly is in the HOME position, execution is switched to subroutine 025, RETRACT 2. The condition in which the "impenetrable object" bit is TRUE AND RETRACT 2 subroutine being active causes screen #62 to be displayed. Screen #62 prompts the operator to exchange the standard filter with a stub filter and press the INSTALL STUB touch switch to install same in the hole created by the BORE 1, subroutine. See RETRACT 2 for more details.

17. SAMPLE 1

Subroutine 017 displays screen #48 which depicts an elapsed time numerical display. The DVS PLC starts a 330 second timer, a 120 second timer, opens solenoid valve V6, and initiates a relay contact closure that starts the gas chromatograph sample/analysis cycle. Valve V6 is opened to enable the GC vacuum pump to draw a sample of the head space gases into the GC. After 120 seconds, valve V6 is closed.

Under normal condition the sample/analysis process requires 5 minutes or 300 seconds. When the 330 second timer times-out, screen #49. Screen #49 instructs the operator to focus attention on the GC computer monitor and determine whether or not the analysis has detected explosive concentrations of the targeted gases. If an alarm condition exists, the operator is to instructed to evacuate/purge the drum by pressing EVAC/PURGE. When pressed EVAC/PURGE will switch execution to subroutine 018, EVACUATE 1. If an alarm condition does not exist, the operator is instructed to press INSTALL such that execution switches to the subroutine that installs filters into the drum lid, INSTALL 1.

ERROR CONDITIONS

A. None foreseen.

18. EVACUATE 1

Subroutine 018's purpose is to evacuate the explosive headspace gases from the drum by closing valves V6, V5, and V4, if not already closed, and opening valve V3. The PLC also turns ON the DVS vacuum pump such that the explosive gases are removed by vacuum suction and vented into the HEPA filter air handling train. The drum's internal pressure is monitored via pressure transmitter P1. When the drum's internal pressure is reduced below an operator presettable setpoint value OR 120 seconds elapses since the start of the evacuation cycle, which ever comes first, execution will switch to subroutine 019, EVACUATE 2.

19. EVACUATE 2

Subroutine 019 displays screen #52 and a PURGE touch switch. Since the EVACUATE 1 subroutine step is not PASS/FAIL, only one option is provided—PURGE. Pressing PURGE 1 causes execution to switch to subroutine 020, PURGE 1.

20. PURGE 1

Subroutine 020's purpose is to inject nitrogen into the headspace volume of the drum and thereby replace explosive head space gases with an inert one. Screen #53 is displayed. The PLC accomplishes the purging task by first setting the nitrogen electropneumatic pressure regulator to 1 atmosphere or 14.7 PSIA. Secondly, the PLC closes valves V6, V3, and V4, if not already closed, and opens valve V5. With valve V5 open, nitrogen flows into the drum head space volume. If the drum's internal pressure rises above 1 atmosphere OR 120 seconds elapses since the start of the purge cycle, which ever comes first, execution switches to subroutine 021, PURGE 2.

21. PURGE 2

Subroutine 021 displays screen #54 and two touch switches, SAMPLE and EVACUATE. If SAMPLE is pressed, execution will switch back to subroutine 017, SAMPLE. If EVAC is pressed, execution will switch back to subroutine 018, EVACUATE 1. It is assumed that the operator will either repeat the EVAC/PURGE cycle and/or execute the SAMPLE subroutine until the explosion hazard has been neutralized. When the explosion hazard has been neutralized, screen #49, which displays after the head space gases have been analyzed, will enable the operator to progress to the install filter step.

22. INSTALL 1

Subroutine 022 displays screen #55, INSTALL FILTER IN PROGRESS. INSTALL 1 causes the linear drive to execute a linear motion sequence that slowly lowers the filter/socket assembly until the filter housing threads are in contact with the rim of the hole in the drum lid. When contact is made, the PLC commands the nutrunner controller to spin the filter/socket assembly at 1 RPM. Since there are 14 threads per inch on the filter housing, the 1 RPM rotation rate of the socket dictates that the downward velocity of the linear drive to be 1/14 th of an inch per second.

Since the threading torque is considerably less than torque required to seat the filter gasket against the drum lid, the preset, programmable, target seating torque will not be achieved until the gasket is seated. When seated properly, the nutrunner will issue two outputs, CYCLE COMPLETE and CYCLE OK, become logic TRUE. If both outputs are TRUE, execution will switch to subroutine 023, INSTALL 2. If 18 seconds elapses since the start of the nutrunner socket rotation AND CYCLE COMPLETE and CYCLE OK are logic FALSE, execution will switch to subroutine 023, INSTALL 2. Finally, if during the execution of INSTALL 1 the linear drive FAULT output goes TRUE because an impenetrable object has been encountered, execution will switch to subroutine 023, INSTALL 2.

23. INSTALL 2

Subroutine 023 displays the results of the filter installation step. Since the threading torque is considerably less than torque required to seat the filter gasket against the drum lid, the preset, programmable, target seating torque will not be achieved until the gasket is seated. If the seating torque is within the HIGH TORQUE and LOW TORQUE limits, the nutrunner will make its CYCLE COMPLETE and CYCLE OK logic outputs TRUE. In response, the PLC will display screen #56, FILTER INSTALLED. Screen #56 displays a RETRACT touch switch, which when pressed, causes execution to switch to subroutine 024, RETRACT 1.

ERROR CONDITIONS

A. The filter housing threads strip-out such that the higher, target seating torque, is never achieved. In this instance, CYCLE COMPLETE and CYCLE OK never go logic TRUE within the 15 second installation time period. The PLC displays screen #57, INSTALL FILTER ERROR 1. The object is to instruct the operator to raise the powerhead assembly to the HOME position so that the standard filter may be exchanged with a stub filter. It is assumed that the slightly larger diameter threads of the stub filter will enable it to be installed when the standard filter could not be. A RETRACT touch switch is displayed on screen #57, which when pressed, switches execution to subroutine 024, RETRACT 1, which retracts the powerhead to the HOME position.

B. An impenetrable object obstruction blocked the downward movement of the filter tip. In this instance, the FAULT output of the linear drive goes TRUE when the position error in the linear drive controller becomes excessive. In response, the PLC displays screen #58, INSTALL FILTER ERROR 2. Screen #58 informs the operator of the impenetrable object encounter, to raise the powerhead to HOME, and exchange the standard filter with a stub filter. A RETRACT touch switch is displayed on screen #58, which when pressed, switches execution to subroutine 024, RETRACT 1, which retracts the powerhead to the HOME position.

C. The stub filter housing threads strip-out such that the higher, target seating torque, is never achieved. In this instance, the recommended course of action is to raise the powerhead to the HOME position, lower the drum, and manually secure the filter to the drum lid via an approved adhesive, such as RTV. If, during the installation of a stub filter, CYCLE COMPLETE and CYCLE OK never go TRUE, the PLC will display screen #59, STUB FILTER INSTALL ERROR 1. A RETRACT touch switch is displayed, which when pressed, causes execution to switch to subroutine 024, RETRACT 1.

24. RETRACT 1

Subroutine 024 displays screen #60, RETRACT POWERHEAD IN PROGRESS. The PLC commands the linear drive to execute linear motion sequence 2, GO HOME, such that the powerhead assembly ascends to the fully raised position. When the movement has successfully terminated, the PLC will switch execution to subroutine 025, RETRACT 2.

25. RETRACT 2

Regardless of the particular sequence of events that cause this subroutine to be active, screen #61 is always displayed when the powerhead arrives at the HOME position. Screen #61 informs the operator of the powerhead's HOME position and that pressing the CONTINUE touch switch will appropriately advance the process. Under normal circumstances, when a standard filter has installed properly, an "installed properly bit" is SET. The logically AND of the CONTINUE touch switch bit AND the "installed properly bit" causes execution to switch to subroutine 027, LOWER DRUM.

ERROR CONDITIONS

A. Impenetrable Object Encountered.

If an penetrable object is encountered a specific bit is SET to record the event. Pressing CONTINUE when the "impenetrable object" bit has been SET will cause screen #62, IMPENETRABLE OBJECT, to be displayed. If an impenetrable object was encountered, the operator is advised to exchange the standard filter with a stub filter, and press the INSTALL STUB touch switch to install same. Execution will switch to subroutine 022, INSTALL 1.

B. Stub Filter Time-out.

If the stub filter strips-out during INSTALL 1, a particular bit will have been SET. Pressing CONTINUE after a stub filter strip-out causes the PLC to display screen #63, STUB FILTER INSTALLATION TIME-OUT. Pressing the LOWER DRUM touch switch on screen #63 will cause the LOWER DRUM subroutine to execute. The intent is to lower the drum with the unseated stub filter still in the drum lid so that it may be manually secured with an adhesive.

C. Standard Filter Time-out.

If the standard filter strips-out during INSTALL 1, a particular bit will have been SET. Pressing CONTINUE after a standard filter strip-out causes the PLC to display screen #65, STANDARD FILTER TIME-OUT. Screen #65 advises the operator to exchange the standard filter with a stub filter, and press the INSTALL STUB touch switch to install same. Execution will switch to subroutine 022, INSTALL 1.

27. LOWER DRUM 1

Subroutine 027 displays screen #67, LOWER DRUM IN PROGRESS. The PLC configures the DVS valves to allow the air actuator to deflate, which in turn, permits the drum to lower under its own weight. As the drum descends, photosensor transmitter beams, one and two, will once again be able to illuminate their respective photosensor receivers. When the lowest photosensor outputs a logic TRUE AND the weight load cell output is below 50 lbs., execution will switch to subroutine 028, LOWER DRUM 2.

28. LOWER DRUM 2

Subroutine 028 displays screen #68, DRUM LOWERED. Screen #68 will always be displayed. The only option is to proceed to the SURVEY subroutine step.

29. SURVEY 1

Subroutine 029 displays screen #70, SURVEY DRUM LID. Screen #68 displays a READY lamp and an UNLOAD touch switch. The operator is instructed to open the access door and wait for the READY lamp to light. In the interim, the PLC is commands the HEPA filter blower motor to increase its rotational speed to 62:5 RPM. After 15 seconds, the blower motor will certainly have reached the setpoint rotational speed. The READY lamp will light indicating that the air flow through the access door is sufficient high to permit the safe surveying of the drum lid.

The operator(s) may take as much time as is required to obtain a survey sample. When the survey operation is complete, the operator presses the UNLOAD touch switch and execution will switch to subroutine 030, UNLOAD DRUM 1.

ERROR CONDITIONS

A. A Stub Filter has Strip-out During the Installation Step.

In this instance, the process would unfold in a manner identical to that which is described above under SURVEY 1. However, if a stub filter has stripped-out screen #73 will display. Screen #73 is identical to screen #70 with the exception that the operator is instructed to manually tighten or apply an adhesive to the stripped-out stub filter. When the survey and stub filter seating operations have been completed, the operator presses the UNLOAD touch switch and execution will switch to subroutine 030, UNLOAD DRUM 1.

30. UNLOAD DRUM 1

Subroutine 030 displays screen #71, UNLOAD DRUM IN PROGRESS. The DVS PLC commands the HEPA filter blower motor to resume its high rotational speed of 73 to 75 Hz. The speed change is assumed to require 15 seconds. After 15 seconds, execution automatically switches to subroutine 031, UNLOAD DRUM 2.

31. UNLOAD DRUM 2

Subroutine 031 displays screen #72, UNLOAD DRUM DONE. Screen #72 instructs the operator to open the cabinet door and remove the vented drum from the DVS cabinet. When the drum unload task is completed and the operator presses the CONTINUE touch switch, execution will switch to subroutine 001, CHANGE, enabling the processing of the next drum. In this way the operator may process a succession of drums. process may be repeated. Pressing the EXIT touch switch causes the EXIT subroutine, subroutine 032 to be active.

32. EXIT

Subroutine 032 displays screen #74, EXIT. Screen #74 provides instructions as to how to end the drum venting session. When the instructions are executed electrical power to the DVS will be switched OFF so no touch switch is required.

II. LINEAR DRIVE HEXADECIMAL TO BINARY CONVERSION

MOTION SEQUENCE DEFINITION SEQUENCE ORDER DURING FILTER INSTALLATION: {5,1,7,4,12,8}

| Bit Address @ C002 | (5) HTM | (1) TM | (7) TT Point | (4) BORE | (12) BTSD | (8) BTS | (6) SBTSD Stub |
|---|---|---|---|---|---|---|---|
| 00208 | 0 | 0 | 0 | 0 | 0 | 0 | 000 |
| 00209 | 1 | 1 | 1 | 0 | 0 | 0 | 100 |
| 00210 | 0 | 0 | 1 | 0 | 1 | 0 | 010 |
| 00211 | 1 | 0 | 1 | 1 | 0 | 0 | 011 |
| 00212 | 0 | 0 | 0 | 0 | 0 | 11 | 000 |
| 00213 | 0 | 0 | 0 | 0 | 1 | 0 | 100 |
| 00214 | 0 | 0 | 0 | 0 | 0 | 0 | 000 |
| 00215 | 0 | 0 | 0 | 0 | 0 | 0 | 000 |

| SEQ# | HEX INPUT TO WORD C002 | TRANSLATION |
|---|---|---|
| Seq #5 = | 0A00 = | 3.50" |
| Seq #1 = | 0200 = | 0.60" |
| Seq #7 = | 0E00 = | 4.25" |
| Seq #4 = | 0817 = | 0.040" |
| Seq #12 = | 2417 = | 1.850" |
| Seq #8 = | 1012 = | 0.667" |
| Seq #6 = | 0C00 = | 2.090" |
| Impenetrable Object | | |
| Kill Motion | Input 6 - Function C (KILL) | |
| Linear Drive Discrete Input | Input 7 - Function S (GO HOME) | |

III. SUBROUTINE SWITCH CONDITIONS

MAIN

1. Defines status controL and notify bits for PT.
2. Defines ON and OFF hits. 51101 & 51102.
3. Defines analog I/D module parameters, if required.
4. Displays screen #1.
5. Sets hit 30000.
6. Compares last subroutine number in HOO to #0032, last sub. number.
7. If equal or (25506=ON), set 30204.
   A. Set 30204
   B. H00→H02
   C. H01→H03
   D. #0000→H00
   E.
8. If not equal or (25507/25505)=ON), jump to series of subroutine calls that are initiated by touch switch hit activation.
9. Set 30000=ON
10. When timer 202=OFF, subroutine calls are enabled., subroutine 000 active.
    A. TIM202=ON (SUB N)
    B. Timer 202=OFF (Initialize)
    C. 30000=ON

STARTUP

1. Start 15 sec timer TIM016.
2. Start 30 sec timer TIM199.
3. If TIM 016=OFF, do the following:

A. Start TIM017 (0.5 Sec)
B. #0000→H00
C. #000→330
D. #0001→H01

4. If TIM016=ON, TIM199=OFF, and 30204=ON, do the following:
   A. Start TIM200 (0.5 Sec)
   B. Display screen #2, #0002→330
   C. #0002→H01
   D. Set 30204
   Display screen #2 after 15 sec and before 30 seconds.

5. If 30203=OFF, 30204=ON, 30205=OFF, and 51104=OFF, do the following:
   A. Start TIM201 (0.5 Sec)
   B. Display screen #3, #0003→330
   C. #003→H01
   D.

6. If 30203=ON, or 30205=ON, or 30204=OFF, do the following:
   A. Start TIM193 (0.5Sec)
   B. Display screen #4, #0004→330
   C. #0004→H01
   D. Start TIM018 (1.0Sec) SR Timer
   E. Start C511 (600), decrementing TIM018
   F. When C511=ON, set 51104

7A. 30000=ON and 30203=OFF, do the following:
   A. Start T130 (0.5) & TIM131 (1.55)
   B. 00209=0 (51102=OFF)
      00210=1
      00211=0
      00212=0
   Linear drive executes back-up home.

STARTUP (000)

7. If TIM016=ON (15 Sec) and 51104=ON (C511=ON), do the following:
   A. 51104=ON (10Min) and 30203=ON (Resume), compare H02 to #0001.
   B. If compare 25506=ON and 51104=ON and 30203=ON (OR) Last Subroutine=30001
      30204=OFF and 51104=ON (OR) Begin @30001
      30205=ON (Begin)→Set 30001 Default start @30001
   C. 51104=ON (10Min) and B0203=ON (Resume), compare H02 to #0002
   D. 51104=ON (10Min) and 30203=ON (Resume) and 25506=ON (Equal), Set 30002
   E. Repeat C and D for the entire subroutine range 0001→0031.

8. If 30000=ON (Sub 000) and 30203=OFF (Resume), do the following:
   A. Start TIM130 (0.1 Sec) and TIM131 (1.0Sec), to generate @1 Sec logn pulse (ON).
   B. Impress or output 0010 on 00209–00212. To cause linear drive to back-up home.

CHANGE (001)

1. If 30001, Set 30001.
2. Start TIM019 (1.0Sec), (30001=ON).
3. If TIM019=OFF, do the following:
   A. Start TIM192(0.5Sec), (30001=ON)
   B. If TIM192=ON, #0005→330
   C. If TIM192=ON, #0005→H01
4. If 30002=OFF, do the following:
   A. Start TIM020 (0.5Sec) SR Timer
   B. If TIM020=ON, [340]→H01
5. If 30002=ON, Set 30002.
6. If 30002=ON, Reset 30001.

INSERT

1. If 30002=ON, Set 30002.
2. If 30002=ON, Start TIM220 (1.0Sec).
3. If TIM220=OFF, do the following:
   A. Start TIM021 (0.5)
   B. #0002→H00, TIM021=ON
   C. #0024→330, TIM021=ON
   D. #0024→H01, TIM021=ON
4. If 30003=ON, Set 30003.
5. If 30003=ON, Reset 30002.

LOAD

1. If 30003, Set 30003.
2. If 30003, start TIM217 (1.0Sec).
3. If TIM217=OFF, do the following:
   A. If 30003, start TIM024=(0.5Sec)
   B. If TIM024=ON, #0003→H00
   C. If TIM024=ON, #0025→330
   D. If TIM024=ON, #0025→H01
4. If 30004=ON (Next Sub) and 00000=OFF (OR)
   30004=ON (Next Sub) and 00001=OFF (OR)
   30004=ON (Next Sub) and 00002=OFF, Set 51106.
   (There is a door open) and/or no drum.
5. If 51106=ON, do the following:
   A. If 30004=ON, Reset 30004
   B. If 51106=ON, #0026→330
   C. If 30003=ON, Start TIM218 (0.5Sec)
   D. If TIM218=ON, #0026→330
   E. If TIM218=ON, #0026→H01
   F. If TIM218=ON, Start TIM025 (15.0 Sec)
   G. If TIM025=ON, #0025→330
   H. If TIM025=ON, #0025→H01
   I. If TIM025=On, Reset 51106

LOAD

6. If 30004/00000/00001/00002=ON, Set 30004.
7. If 30004/00000/00001/00002=ON, Set 30003.

INITIAL 1

1. If 30004, Set 30004.
2. If C509=OFF, do the following:
   A. CMP H02 to #0004 (Init1)
   B. 25506=ON, Set 51108 (Last=0004)
   C. If 30004=ON (012) 30203=ON (Resume), start TIM026 (0.5Sec).
   D. If TIM026=ON, C509=ON (1)
   E. If TIM026=ON, #027→330
   F. If TIM026=ON, #027→H01
   G. If TIM026=ON, #0000→DM0040
      DM 0041
      DM 0042
      DM 0043
   H. If TIM026=ON, DM0004→DM0043 Compute upper and lower compare limits.
3. If 51109=OFF, do the following:
   A. Start SR Timer, TIM027 (3.0 Sec)
   B. If TIM51101=ON, turn ON 00402 (Blower).
   C. If TIM027=ON, compute motor speed output work (binary).→160.
   D. If TIM027=ON, 147→DM0047, read the differential pressure transmitter.
   E. If TIM027, area compare DM0047.
   F. If TIM027, C510 (21) decrements.
   G. If TIM027, 25507=ON, subtract a step from the blower speed. DM0048→160.
   H. 25506=ON and 30203=Off (OR)

25507=ON and 30203=OFF (OR)
51108=ON and 30203=ON, set 51109.

Set the blower speed with respect to the differential pressure (cabinet) transmitter.

4. If 51109=ON, do the following:
  A. Start TIM204 (0.6 Sec).
  B. If TIM204=ON, #0028→330.
  C. If TIM204=ON, #0028→H01.
  D. C510=ON (63 Sec) and 30203=OFF (OR) C51020N and 30203=ON and 51108, Set 51110.
    If 51109=ON, motor up to speed, display screen #28.
    If 51110=ON the motor did not come up to speed in 63 seconds.
  E. Start TIM204 (0.6 Sec).
  F. If 51110=ON, start TIM205 (0.6 Sec).
  G. If TIM205 (=ON), #0075→330.
  H. If TIM205 (=ON), #0075→H01.
  I. If 30203=ON, and 51109=ON (OR) 30005=ON, Set 30005. Reset 30004.

INITIAL 2

1. 30005=ON, Set 30005 30203=ON, call sub 4.
2. 30005=ON, Start TIM222 (0010).
3. If TIM222=OFF, do the following:
  A. If 30005, Start TIM028 (0.5Sec).
  B. TIM028=ON, H03→330.
  C. TIM028=ON, H03→H01.
  D. TIM028=ON, H02→H00.
  E. TIM028=ON, 340→330.
4. If 30006=On, Set 30006.
5. If 30006=On, Reset 30005.

WEIGH 1

1. 30006=ON, Set 30006.
2. 30203=ON, Call Subf 4 (Start and bring motor to speed).
3.
4. 30006=ON, Reset 30203. (Resume).
5. If TIM225=ON, do the following:
  A. If TIM029=ON, #006→H00.
  B. If TIM029=ON, #0029→330.
  C. If TIM029=ON, #0029→H01.
  D.
6. If 30007=ON, Set 30007.
7. If 30007=ON, Reset 30006.

WEIGH 2

1. 30007=ON, Set 30007.
2. 30203=ON, Call Sub #4.
3. 30007=ON, Reset 30203 (Resume).
4. If C508=Off (001) (LOOPCNT), do the following:
  A. 30007=ON, Start TIM030 (0.5Sec).
  B. 30007=ON, Start TIM033 (1.0Sec).
  C. TIM030=ON, C508=ON.
  D. TOM030=ON, Display and store #0030 in 330 and H01.
  E. Initialize DM005–54.
  F. If TIM030=ON and 51111=OFF (Drum Weighed), start 70.0 Sec Timer. (TIM031).
5. If 51111=OFF (Drum Weighed), do the following:
  A. Start SR Timer, TIM032 (4.0 Sec).
  B. If 0006=ON (Photocell #1), turn on output 00301 (Open solenoid value V1).
  C. If 0000=OFF (Logic output of pressure regulator #1, ON when SC=PV), do the following:
    a. Start TIM032 (4.0 Sec)=ON, #0020 (BIN)+ DM0050→DM0051.
    b. Start TIM032 (4.0 Sec)=ON, DM0051→DM0050 move the digital equivalent of 1 PSIG into DM0051, update DM0050.
    c. Start TIM032 (4.0 Sec)=ON, DM0051→161 output new pressure command to PREG1.
    d. TIM032=ON, 145→DM0052. Read analog input of weight load cells.
    e. TIM032=ON, Compare weight to 50 lbs.
    f. TIM032=ON, and 25505=ON, (Greater than) Set 30210.
    g. TIM032=ON, and 25505=ON, Area compare current sample weight to past sample upper and lower limit.
    h. 0006=OFF (Photo cell off) and 25505=ON (G.T.) (OR)
       0006=OFF and 25506=ON, (TO), (OR)
       T031=ON (70.0 Sec).set 51111.
6. If 51111=ON, (Drum weighed or Time-Out), do the following:
  A. 5111=ON, Reset 30210 (Greater than 50 lbs).
  B. 5111=ON, 00301=OFF (Turn off valve V1).
  C. TIM215=ON (0.5Sec).(Start).
  D. TIM215=ON (0.5Sec), #0008→H00 (Update Sub#).
  E. TIM215=ON (0.5Sec), Compare drum weight DM0052 to 1200?
  F. 25505 (GT), #0032→330 and H01. (Drum to heavy screen).
  G. 25506 (EQ) OR 25507=ON, and TIM215=ON, #0031→330 and H01. (Good Screen).
  H. TIM031=ON (70 Sec) and 30210=OFF (Wt<50 lbs), #0033→330 and H01. (Time-out Screen).
7. 51111=ON, Set 30008.
8. 51111=ON, Reset 30007.

WEIGH 3

1. 30008=ON, Set 30008.
2. 30203=ON, Call Sub #004.
3.
4. 30203=ON, Start TIM035 (1.0 Sec).
5. TIM035=ON, do the following:
  A. Start TIM034 (0.5).
  B. #0008→H00.
  C. #H03→330.
  D. #H01→H01.
6. 30009=ON, Set 30009.
7. 30009=ON, Reset 30203.
8. 30009=ON, Reset 30008.

RAISE 1

1. 30009=ON, Set 30009.
2. 30203=ON, Call Sub #004.
3. 30009=ON, Reset 30203.
4. TIM037=ON, (1.0 Sec), do the following:
  A. #0009→H100 (Update Sub#).
  B. #0034=330 (Display Screen #34).
  C. #0034→H01 (Store Screen #34).
5. 51113=OFF, (Drum not raised to seal), do the following:
  A. Start 70.0 Sec Timer (TIM038).
  B. Start SR timer (TIM039) (4.0 Sec).
    a. calculate upper and lover limits of seal force every 4.0 sec.
    b. 00007=ON and 51113 OFF, open valve V1by turning ON 00301. 00008 is photocell #2.
    c. 00007=OFF and 25505=ON (OR) 00007=OFF and 25506=ON (OR) 00007=ON TIM038=ON (70.0 Sec), Set 5111 B. (Drum raised to seal).

6. 51113=ON (Drum Raised), do the following:
   A. (Turn offV1) 51113=ON, 00301→OFF.
   B. Start TIM216 (0.5).
   C. TIM216=ON, #0010→H00.
   D. TIM216=ON, #0035→330.
   E. TIM216=ON, #0035→H01.
   F. TIM21620N and 51113=OFF and TIM038, #0036→330.
   G. TIM21620N and 51113=OFF and TIM038, #0036→H01.
7. 30010=ON, Set 30010.
8. 30010=ON, Reset 30009.

RAISE2
1. 30010=ON, Set 30010.
2. 30203=ON, (Resume), Call (Sub#4).
3.
4. 30203=ON, Start TIM229 (1.0).
5. TIM210=OFF, do the following:
   A. Start TIM041 (0.5).
   B. H02→H00.
   C. H03→330.
   D. H03→H01.
6. 30011=ON, Set 30011.
7. 30011=ON, Reset 30010 OR
8. 30111=ON, Set 30111. 30111=ON, Reset 30203.
9. 30111=ON, Reset 30010.

LOWER PH 1
1. 30011=ON, Set 30011.
2. 30203=ON, (Resume), Call Sub #004.
3. 30203=ON, (Resume), Execute back-up to home linear drive program.
4. 30011=ON, Reset 30203.
5. C506=OFF (SV=1), do the following:
   A. Start TIM042 (0.5Sec).
   B. TIM042=ON, #0011→H00.
   C. TIM042=ON, #0037→330.
   D. TIM042=ON, #0037→H01.
   E. TIM042=ON, Reset 51114, 51115, 51000.
6. 30203=Off (Resume) and C506=ON (SV=1, PV=), and 51114=OFF, do the following:
   A. Start TIM043 (0.5Sec).
   B. Start TIM044 (1.5 Sec).
   C. TIM043=ON and TIM044=OFF (OR) 00102=ON, output 00209=ON
      51102=OFF, output 00210=OFF
      TIM043=ON and TIM044=OFF (OR) 00102=ON, output 00211=ON
      51102=OFF, output 00212=OFF.
   D. 00101=ON, Set 51115.
   E. TIM043=ON, TIM045 (5.0) Starts.
   F. TIM044=ON (1.5 Sec) and 00102=Off and 51115=ON Motion), Set 51114. Linear Motion PRGM #0101 has terminated.
   G. TIM045=ON and 51115=OFF, JMP 19, to time-out error message @ end of subroutine. Linear Motion PRGM 0101-Done.
7. 51114=ON, Set 51000. (This is a linear motion program identifier, like 51114).
8. 30203=OFF and C506=ON and 51000=OFF, do the following:
   A. Start TIM 046 (0.5Sec), if 30010=ON.
   B. Start TIM047 (1.5 Sec), if 30010=ON.
   C. TIM046=ON and TIM047=OFF (OR) 00102=ON,
      a. Turn ON output 00304, V4 Open.
      b. Turn ON output 00401, Vacuum Pump ON.
      c. Start SR Timer TIM048 (0.5Sec).
   D. TIM048=ON, 146 (Force)→DM0070.
   E. TIM048=ON, Compare DM0070 (Force) to 10 lbs.
   F. TIM046=ON and TIM047=OFF and 25507=ON, output 00209=ON.
      TIM046=ON and TIM047=OFF and 25507=ON, output 00210=ON.
      TIM046=ON and TIM047=OFF and 25507=ON, output 00211=ON.
      51102=OFF, output 00212=OFF, Executes linear motion program #0111.
   G. 00101=ON Motion), Set 51001.
   H. TIM046=ON, Start TIM049 (5.0Sec).
   I. 51102=OFF, output 00200=OFF.
      51102=OFF, output 00201=OFF.
      51102=OFF, output 00202=OFF.
      51102=OFF, output 00203=OFF.
      51102=OFF, output 00206=ON.
   Executes notary motion program #00001.
   J. TIM049=ON and 51001=OFF (No Motion). JMP to time-out error messages @ end of subroutine.
   K. TIM047=ON and 00102=OFF and 51001=ON Motion Occurred), Set 51000.
9. 51000=ON, Compare DM0070 (Force) to 4 lbs.
10. 51000=ON and 25507=ON, #0039→330.
11. 51000=ON and 25507=ON, #0039→H01.
12. 51000=ON and 25506=ON (OR) 25505=ON, #0038→330.
13. 51000=ON and 25506=ON (OR) 25505=ON, #0038→H01. Display and store good message screen.
14. 51000=ON and 25506=ON (OR) 25505=ON, Set 30012.
15. 51000=ON and 25506=ON (OR) 25505=ON, #0012→H00.
16. TIM045=ON and 51115=OFF (OR) TIM049=ON and 51001=OFF, #0024→H00.
17. TIM045=ON and 51115=OFF (OR) TIM049=ON and 51001=OFF, #0076→330.
18. TIM045=ON and 51115=OFF (OR) TIM049=ON and 51001=OFF, #0076→H01.
19. 30011=ON, Compare 340 to #0038.
20. 25506=ON, Set 30012. 25506=ON, Reset 30011.
21. 30011=ON, Compare 340 to #0039.
22. 25506=ON, Set 30012. 25506=ON, Reset 30011.
23. 30011=ON, Compare 340 to #0076.
24. 25506=ON, Set 30012. 25506=ON, Reset 30011.

LOWER PH2
1. 30012=ON, Set 30012.
2. 30203=ON, Call Sub #4.
3. 30012=ON, Start TIM050 (0.5).
4. TIM050=ON, H02→H00.
5. TIM050=ON, H03→330.
6. TIM050=ON, H03→H01.
7. 30013=ON, Set 30013.
8. 30106=ON, Set 30106.
9. 30108=ON, Set 30108.
10. 30013=ON (OR) 30106=ON (OR) 30108=ON, Reset 30012.

SEALTST 1
1. Initialize and call subroutine 4 if 30203=ON.
2. 30013=ON, Start TIM232 (1.05 Sec)

3. TIM232=OFF, do the following:
   A. Start TIM051 (0.5Sec).
   B. TIM051=ON, #0013→H00.
   C. TIM051=ON, #00040→330.
   D. TIM051=ON, #0040→H01.
   E. TIM051=ON, Start TIM053 (60.0 Sec).
4. 51002=OFF a nd 51003=OFF, do the following:
   A. Start SR Timer, TIM055 (1.0 Sec).
   B. TIM055=ON, C504 decrements (SC=60).
   C. TIM055=ON, @ DIV C504/#0060→DM0080.
   D. TIM055=ON, 148→DM0082.
   Read pressuretransmitter output @ address 148.
   E. TIM055=ON, Compare DM0082 to DM0001. The seal test EVAC pressure constant.
   F. 25505=ON and TIM053=OFF, open valve V3by turning ON output 00303.
   G. 25505=ON, vacuum pump ON (00401).
   H. (25506=ON (OR) 25507=ON) and TIM053=OFF, Set 51002.
   I. 25505=ON and TIM053=ON, Set 51003.
5. 51002=ON (OR) 51003=ON, do the following:
   A. Start TIM234 (0.5Sec).
   B.
   C. 51002=ON and TIM234=ON, #0014→H00.
   D. 51002=ON and TIM234=ON, #0041→330.
   E. 51002=ON and TIM234=ON, #0041→H01.
   F. 51003=ON and TIM234=ON, #0042→330.
   G. 51003=ON and TIM234=ON, #0042→H01.
   H. 30013=ON, Compare 340 to #0041.
      Set 30014.
      Reset 30013.
   I.

SEALTST 2
1. Initialize and call sub #004.
2. TIM056=ON (0.6 Sec).
3. H02→H00.
4. H03→330.
5. H03→H01.
6. 30015=ON (Bore), Set 30015.
7. 30111=ON (Lower), Set 30111.
8. 30108=ON (Retract), Set 30108.
9. 30015=ON (OR) 30111=ON (OR) 30108=ON, Reset 30014.

BORE 1
1. Initialize and call sub #4 if 30203=ON.
2. 30015=ON, Start TIM058 (1.0 Sec).
3. TIM058=OFF (1.0 Sec), do the following:
   A. Start TIM057 (0.5 Sec)
   B. TIM057=ON, C503=ON (SV=1).
   C. TIM057=ON, #0015→H00.
   D. TIM057=ON, #0045→330.
   E. TIM057=ON, #0045→H01.
   F. TIM057=ON, Reset 51004.
   G. TIM057=ON, Reset 51005.
   H. TIM057=ON, Reset 51006.
   I. TIM057=ON, Reset 51007.
   J. TIM057=ON, Reset 51008.
   K. TIM057=ON, Set
   Display screen #45, update sub #, initialize.
4. TIM059=OFF (200 Sec) and C501=OFF (SV=100), do the following:
   A. 30015=ON, Start TIM059(2005).
   B. 50908=ON, Start TIM060(15?).
   C. TIM060=ON, Reset (50908).
   D. TIM060=ON, Start TIM061 (30?).
   E. TIM061=ON, Set (50908) generates a 15? and 305 OFF pulse.
   F. 50907=ON, Start TIM062 (15).
   G. TIM062=ON, Reset (50907).
   H. TIM062=ON, Start TIM063 (25).
   H. TIM063=ON, Set 50997 generate a 15 ON and 15 OFF pulse.
   J. 25502=ON, C502 (SV=200) decrements.
   K. 25502=ON, @ DIV C502/#0060→DM0083. Generate decrementing clock time output. DM0083 & DM0084.
   L. TIM060=OFF and C502=OFF, output 00206ON. Turn ON nutrunner.
   M. 51101=ON, output 00200 ON.
      51101=ON, output 00201 ON.
      51101=ON, output 00202 ON.
      51102=OFF, output 00203 OFF.
   N. 25502=ON, Calculate.
      a. 1/20 th of the bore force, 40 lbs.
      b. Upper and lower limits of 95% and 105%.
      c. A rea compare.
   O. 25507=ON, do the following:
      a. 25507=ON, Set 51004.
      b. 00209=0.
         00210=0.
         00211=1, 25507=ON.
         00212=0.
   P. 25506=ON, Set 51005.
   Q. 25505=ON, do the following:
      a. 25505=ON, Set 51006.
      b. 00209=1, 25505=ON.
      c. 00210=1, 25505=ON.
      d. 00211=1, 25505=ON.
      e. 00212=1, 25505=ON.
   Execute back-up, linear motion program #1111.
   R. 25502=ON, Compare bore forceto 10 lbs.
   S. 50700=OFF (83 gal w/out lid), do the following:
      a. (51005=ON (OR) 51004=ON) and 25507=ON, 25502, Decrement C501(SV=100).
   T. 50700=ON (83 Gal w/lid), do the following:
      a. (51005=ON (OR) 51004=ON) and 25507=ON and 25502, Decrement C480 (SV=150).
5. TIM059=OFF and C501=ON. (OR)
   TIM059=ON and C501=OFF. (OR)
   TIM059=OFF and C480=ON. (OR)
   TIM059=ON and C480=OFF, #0016→H00.
   If not time-out (200?) and C501down by 100 (to sampling point) or equivalent for 83 gal w/lid, update sub #.
6. T059=OFF (OR) C480 and C501=ON, #0046→330.
7. T059=OFF (OR) C480 and C501=ON, #0046→H01.
8. T059=ON (OR) C480 and C501=OFF, #0047→330.
9. T059=ON and C501=OFF, #0047→H01.
10. T059=OFF and C501=ON. (OR)
    T059=ON and C501=OFF. (OR)
    T059=OFF and C480=ON (OR)
    T059=ON and C480=OFF, Reset 30015.

BORE 2
1. 30100=ON, Set 30100.
2. 30203=ON, Call sub #4.
3. 30100=ON, Start TIM065 (0.5?).
4. TIM065=ON, H02→H00.
   H03→330.
   H03→H01.

5. 30101=ON (Sample) or 30108=ON (Retract), Reset 30100.

SAMPLE
1. 30101=ON, Set 30101.
2. 30203=ON, Call subroutine #4, execute, and ret.
3. TIM235=OFF, (1.0?) do the following:
   A. 30101=ON, Start TIM066 (0.55).
   B. C500→0 ON, TIM066=ON, C500(SC=1).
   C. TIM066=ON, #0017→H00
      #0048→330
      #0048→H01
   Reset 51008
4. 00100=OFF (GC Done) or (TIM067=OFF (300?).
   A. 30101=ON, Start TIM067 (300?).
   B. 30101=ON, Start TIM069 (180?).
   C. TIM070=OFF, Start SR Timer TIM070(1.05).
   D. TIM070=On, C499 (480. decrements.
   E. TIM070=ON, C499/60→DM0090.
   F. 30101=ON, Start TIM068 (2?) Start GC.
   G. TIM069=OFF, Turn ON 00304 (Valve V4).
   H. TIM068=O FF, Turn ON 00307 (GC Start).
   I
5. 0010=ON (GC Done) or T067=ON do the following:
   A. 00100=ON (GC Done), #0049→330.
   B. 00100=ON (GC Done), #0049→H01.
   C. TIM067=ON (and) TIM069 ON, #0050→330.
   D. TIM067=ON (and TIM069=ON, #0050→H01.
   E. 51008=ON, Reset 30101.

EVAC 1
1. 30102=ON, Set 30102.
2. 30203=ON, Call sub#004, execute, ret.
3. 30102=ON, Start TIM238 (0.5?).
4. TIM238=OFF, do the following:
   A. 30102=ON, Start TIM072 (0.5?).
   B. TIM072=ON, #0018→H00.
   C. TIM 072=ON, #0051→330.
      TIM 072=ON, #0051→H01.
      TIM072=ON, Reset 51010.
      TIM072=ON, Reset 51011.
5. 51010=OFF (2 Min Timer), do the following:
   A. Start SR TImer TIM073 (1.0?).
   B. TIM073=ON, C502 decrements down (SV 120).
   C. C502=ON, Set 51010.
   D. TIM073=ON, C502/60→DM0093
      DM0094
   E. TIM073=ON, Read 147 (Pressure) 147→DM0095.
   F. TIM073=ON, Compare 147 (DM0095) to drum evacuate pressure (DM0002) parameter.
   G. 25505=ON, (Greater than), open valve V3, 00303.
   H. 25505=ON, Turn vacuum pump on 00401.
   I. 25507=ON (OR) 25506=ON, Set 51011.
6. 51010=ON, do the following:
   A. 51011=ON, (Evac Pressure Attained),
      #0020→H00.
      #0052→330.
      #005→H01.
   B.

EVAC 2
1. 3010332 ON, Set 30103.
2. 30203=ON, Call sub #4, execute, ret.
3. 30103=ON, Start TIM240 (1.0?).
4. TIM240=OFF, do the following:
   A. 30103=ON, Start 74 (0.55).
   B. TIM240=ON, H02→H00.
   C. TIM240=ON, H03→330.
   D. TIM240=ON, H03→H01.
5. 30104=ON, Reset 30103.

PURGE 1
1. 30104=ON, Set 30104.
2. 30203=ON, Call Sub #004, execute, ret.
3. 30104=ON, Start TIM241 (1.0?).
4. TIN241=OFF, do the following:
   A. 30104=ON, Start TIM075 (0.55).
   B. TIM075=ON, #0021→H00.
   C. TIM075=ON, #0053→330.
   D. TIM075=ON, #0053→H01.
   E. TIM075=ON, Convert DM0003 to Binary.
   F. TIM075=ON, DM0100 (Binary)→170 (Pressure Regulator 2 command signal).
   G.
5. 51013=OFF, do the following:
   A. Start SR TImer TIM076 (1.0?).
   B. TIM076=ON, Decrement C490 (SV=120).
   C. C490=ON, Set 51012.
   D. TIM076=ON, Divide C490/60→DM0101. Clock, min (DM0101), Sec (DM0102).
   E. TIM076=ON, Read pressure 147→DM0103.
   F. TIM076=ON, Compare PV pressure (DM0103). to SV parameter (DM0003).
   G. 25507=ON, and 51012=OFF (Not time-out), turn output 00305 ON. (Turn V5 value on or open).
   H. (25506=ON or 25505) or 51012=ON, Set 51013.
6. 51013=ON, (Pressure attained or time-out), do the following:
   A. 51013=ON, Start TIM242 (0.55).
   B. TIM242=ON, #0022→H00.
      #0054→330.
      #0054→H01.
      Reset 30104.

PURGE 2
1. 30105=ON, Set 30105.
2. 30203=ON, Call sub #004, execute, ret.
3. 30105=ON, Start TIM243 (1.0?).
4. TIM243=OFF, do the following:
   A. Start TIM078 (0.5?).
   B. TIM078=ON, H02→H00.
      H03→330.
      H03→H01.
5. 30102=ON, (Evacuate) or 30101=ON (Sample), Reset 30105.

INSTALL 1
1. 30106=ON, Set 30106.
2. 30203=ON, Call Sub #004, Execute, ret.
3. 30106=ON, Start TIM245 (1.05).
   A. Start TIM080 (0.55).
   B. TIM080=ON, #0022→H00.
      #0055→330.
      #0055→H01.
      Reset 51014.
      Reset 51015.
      Reset 50906.
4. 51015=OFF, do the following:
   A. Start SR Timer TIM081 (1.05).
   B. TIM081=ON, C500 decrements (SV=90).
   C. C500=ON, Set 51014.
   D. TIM081=ON, C500/60→DM0110.
   E. 50906=ON, Start TIM083 (155).
   F. TIM083=ON, Reset 50906.

G. TIM083=ON, Start TIM082 (305).
H. TIM082=ON, Set 50906.
   generate a 155 ON, 305 OFF pulse.
I. 30106=ON, Start TIM084 (0.55).
J. 30106=ON, Start TIM (1.55).
K. TIM083=OFF, (155) and C500=OFF and 00013=OFF (Fault) and 00014=OFF (Cycle Ok) and 00015=OFF (Cycle complete), turbo ON 00206(Nutrunner).
L. 00200=1 (51101=ON).
   00201=1 (51101=ON).
   00202=0 (51102=OFF).
   00203=0 (51102=OFF).
M. T081=ON, 146→DM0110 (Read forcetransducer).
N. T081=ON, Compare DM0110 to #0040 lbs.
O. T084=ON and T085=OFF (OR) 00102 and 25505=OFF,
   00209=1.
   00210=1.
   00211=0.
   00212=1.
P. 00013=ON or 00014 or 00015or 51014=ON or 25505, Set 51015 (Done with install).
Q. 00014=ON or 00015=ON, Set (50905).

5. 51015=ON, do the following:
   A. 51015=ON,.TIM275=0.55, #0023→H00.
   B. 00014=ON and 00015=ON, #0056→330.
   C. 00014=ON and 00015=ON, #0056→H01, If cycle OK and cycle COM, display #0056, screen.
   D. 51014=ON, #0057→330 Time-out. 51014=ON, #0057→H01.
   E. 25505=ON, #0058→330. 25505=ON, #0058→H01.
   F. 51014=ON and 30110=ON (Stub), #0059→330. 51014=ON and 30110=ON (Stub), #0059→H01.
   G. 51015=ON, Reset 30106.

INSTALL 2
1. 30107=ON, Set 30107.
2. 30203=ON, Call sub #004, execute, ret.
3. 30107=ON, Start TIM247 (1.05).
4. TIM247=OFF, do the following:
   A. Start TIM086 (0.55).
   B. TIM086=ON, H02→H00.
   C. TIM086=ON, H03→330.
   D. TIM086=ON, H03→H01.
   E. 30108=ON, Set 30108.
   F. 30108=ON, Reset 30107.

RETRACT 1
1. 30108=ON, Set 30108.
2. 30203=ON, Call sub #004, execute, ret.
3. 30108=ON, Start TIM300 (1.05).
4. TIM249=OFF, do the following:
   A. Start TIM090 (0.55).
   B. TIM090=ON, #24→H00.
      #0060→330.
      #0060→H01.
5. 50800=OFF, do the following:
   A. 30108=ON, Start TIM091 (0.55).
   B. 51102=OFF, 00209=0.
      00210=1.
      00211=0.
      00212=0.
   Back up to home.
   C. (T091=ON and T092=OFF) or 00102=ON, Turn ON output 00305 (Valve V5 to push socket out of housing).
   D. 00101=ON, Motion), Set 50900.
   E. (T091=ON and T092=OFF) or 00102=ON and 50906=OFF, Turn output 00206 ON. Start nutrunner.
      00206=1.
      00200=1.
      00201=0.
      00202=0.
      00203=0.
   F. T091=ON, Start TIM093 (55).
   G. (50900=ON and 00102=OFF) or (00101=OFF and T093=ON), Set 50800.

6. 50800=ON, do the following:
   A. 50900=ON and 00102=ON, #0025→H00.
      50900=ON and 00102=ON, #0061→330.
      50900=ON and 00102=ON, #0061→H01.
   B. 30109=ON and 00102=ON, Set 30108.
   C. 00101=OFF and TIM093=ON, #0076→330.
      00101=OFF and TIM093=ON, #0076→H01.
   D. 30109=ON, Reset 30108.

RETRACT 2
1. 30109=ON, Set 30109.
2. 30203=ON, Call sub #004, execute, ret.
3. 30109=ON, Start-TIM250 (1.05).
4. TIM250=OFF, do the following:
   A. Start TIM100 (0.55) and TIM100.
   B. 30109=ON and 50701=ON, #0065→330.
   C. 30109=ON and 50701=ON, #0065→H01.
   D. 30109=ON and 50702=ON, #0064→330.
   E. 30109=ON and 50702=ON, #0064→H01.
   F. 30109=ON and 50703=ON, and TIM100, #0063→330.
   G. 30109=ON and 50703=ON, and TIM100, #0063→H01.
   H. 30109=ON and 50704=ON, and TIM100, #0062→330. 30109=ON and 50704=ON, and TIM100, #0062→H01.
5. 30203=ON and TIM100=ON, #H02→H00.
   #H03→330.
   #H03→H01.
6. 30110=ON, Set 30110.
7. 30109=ON, and 30111=ON (OR) 30109=ON and 30110=ON, Reset 30109.
8. 30111=ON, Set 30111.

INSERT SB
1. 30110=ON, Set 30110.
2. 30203=ON, Call sub #004, execute, ret.
3. Start TIM251 (1.05).
4. TIM251=ON, do the following:
   A. 30110=ON, Start TIM101 (0.55).
   B. TIM101=ON, #0026→H00.
   C. TIM101=ON, #0066→330.
   D. TIM101=ON, #0066→H01.
5. 30106=ON,. Set 30106.
6. 30106=ON, Reset 30110.

LOWER 1
1. 30111=ON, Set 30111.
2. 30203=ON, Call sub #004, execute, ret.
3. 30111=ON, Start TIM253 (1.05).
4. TIM253=OFF, do the following:
   A. Start TIM102 (0.55).
   B. TIM102=ON, #0027→H00.
      TIM102=ON, #0067→330.
      TIM102=ON, #0067→H01.
   C. 30111=ON, Reset 50805.
5. 50805=ON, do the following:

A. Start SR Timer TIM103 (1.05).
B. TIM103=ON, Read Weight @ 145→DM0110.
C. TIM103=ON, Compare Weight (DM0110) to #0015 lbs.
D. (0006=OFF) and 25505=ON. (OR) (00007=OFF) Open valve V2 by turning ON output 00302.
E. 0006=ON and 00007=ON and 25507=ON, Set 50805.

6. 50805=ON, do the following:
    A. 50805=ON, #0028→H00.
       50805=ON, #0068→330.
    50805=ON, #0068→H01.
    B. 30112=ON, Reset 30111.

LOWER 2

1. 30112=ON, Set 30112.
2. 30203=ON, Call sub #004, execute, ret.
3. Start TIM255 (1.05).
4. TIM255=OFF, do the following:
    A. Start TIM104 (0.55).
    B. 30203=ON, and TIM104, H02→H00.
    C. 30203=ON, and TIM104, H03→330.
    D. 30203=ON, and TIM104, H03→H01.
    E. TIM104=ON, #0068→330.
       TIM104=ON, #0068→H01.
       TIM104=ON, #0028→H00.
    F. 30113=ON, Reset 30112.

SURVEY 1

1. 30113=ON, Set 30113.
2. 30113=ON, Start TIM259 (1.05).
3. TIM259=ON, do the following:
    A. Start TIM105 (0.55).
    B. TIM105=ON, #0029→H00.
    C. TIM105=ON, #0070→330.
    D. TIM105=ON, #0070→H01.
    E. 30113=ON, 50808 (Reset).
4. 30114=OFF, do the following:
    A. 00001=OFF, Start TIM106 (1.05).
    B. 00001=OFF, and TIM106=ON, #0CD0→161.
    Increase motor speed until 100 F/Min velocity results.
    C. TIM106=ON, Start TIM260 (1.05).
    D. TIM260=ON, Set 50808.
    E.
5. 30114=ON, SEt 30114.
6. 30114=ON and 00001=ON, Reset 30113.

UNLOAD 1

1. 30114=ON, Set 30114.
2. 30114=ON, Start TIM (1.05).
3. 30114=ON, Start 261 (1.05).
4. TIM261=OFF, do the following:
    A. Start TIM107 (0.55).
    B. TIM107=ON, #0030→H00.
    C. TIM107=ON, #0071→H01.
    D. TIM107=ON, #0071→330.
    E. TIM107=ON, #0000→161.
5. TIM=ON, do the following:
    A. Start TIM262 (0.55).
    B. TIM262=ON, #0031→H00.
    C. TIM262=ON and 50705=OFF, #0072→330.
    D. TIM262=ON and 50705=OFF, #0072→H01.
    E. TIM262=ON and 50705=ON, #0073→330.
       TIM262=ON and 50705=ON, #0073→H01.
    F. TIM262=ON, Compare 340 to 5.
    G. 30115=ON, Set 30115.

H. 25505=ON, SEt 30001.
I. 30115=ON or 25505=ON, Reset 30114.

UNLOAD 2

1. 30115=ON, Set 30115.
2. 30115=ON, Start T266 (1.05).
3. TIM266, do the following:
    A. Start T110 (0.55).
    B. 30203=OFF and T110=ON, #0031→H00.
    C. 30203=OFF and T110=ON, #0072→330.
    D. 30203=OFF and T110=ON, #0072→H01.
    E. 30203=ON and T110=ON, H02→H00.
    F. 30203=ON and T110=ON, H03→330.
    G. 30203=ON and T110=ON, H03→H01.
    H. 30200=ON, Set 30200.
    I. 30200=ON, Reset 30115.

EXIT 1. 30200=ON, Set 30200.
2. Start TIM270 (1.05).
3. TIM270=OFF, do the following:
    A. TIM111 (0.55).
    B. TIM111=ON, #0032→H00.
    C. TIM111=ON, #0074→330.
    D. TIM111=ON, #0074→H01.
4. TIM270=ON, Rest 30200.

| ANALOG MODULE SETUP | | |
|---|---|---|
| 1. Analog Input Module (AD002) | | |
| Machine # = 4 | | |
| DM1400 = (09) 0 | Alarm Mode 1 | |
| = (08) 1 | BCD (4 - digit) | |
| = (07) 0 | Input 8 Enabled | |
| = (06) 0 | Input 8 Enabled | |
| = (05) 0 | Input 8 Enabled | |
| = (04) 0 | Input 8 Enabled | |
| = (03) 0 | Input 8 Enabled | |
| = (02) 0 | Input 8 Enabled | |
| = (01) 0 | Input 8 Enabled | |
| = (00) 0 | Input 1 Enabled | |
| DM1400 = 0100 | | |
| DM1401 = (15) 1 | DM1401 = AAAA | |
| = (14) 0 | | |
| = (13) 1 | 4-20MA | |
| = (12) 0 | | |
| = (11) 1 | | |
| = (10) 0 | | |
| = (9) 1 | | |
| = (8) 0 | | |
| = (7) 1 | | |
| = (6) 0 | = (01) 1 | |
| = (5) 1 | = (00) 0 | |
| = (4) 0 | | |
| = (3) 1 | | |
| = (2) 0 | | |
| ANALOG MODULE SETUP | | |
| 1. AD002 | | |
| DM1402 = (15) 1 | (07) 1 | |
| (14) 1 | | |
| (13) 1 | DM1402 = FFFF | |
| (12) 1 | | |
| (11) 1 | Sealing & Mean | |
| (10) 1 | ON (Enabled) | |
| (09) 1 | | |
| (08) 1 | (00) 1 | |

-continued

| | | |
|---|---|---|
| DM1403 = 0000 | Roots & Alarms OFF (Disabled) | |
| DM1401 = 0000 | DM1414 = 0000 | |
| DM1405 = 0080 | DM1414 = 0500 | |
| DM1406 = 0000 | DM1416 = 0000 | |
| DM1407 = 0125 | DM1417 = 0005 | |
| DM1408 = 0000 | DM1418 = 0000 | |
| DM1409 = 0125 | DM1419 = 0060 | |
| DM1410 = 0000 | Upper & Lower Limits | |
| DM1411 = 0100 | | |
| DM1412 = 0000 | | |
| DM1413 = 2000 | | |
| ANALOG MODULE SETUP | | |
| 1. AD002 | | |
| DM1420 = 0005 | | |
| DM1421 = 0005 | Sampling Time = @ 250MS | |

-continued

| | | |
|---|---|---|
| DM1422 = 0005 | @ 125MS | |
| DM1423 = 0005 | | |
| DM1424 = 0005 | | |
| DM1425 = 0005 | | |
| DM1426 = 0005 | | |
| DM1427 = 0005 | | |
| 2. DA001 | | |
| Machine codes = 6 & 7 | | |
| DIP Switches SW - 1 = OFF | | |
| - 2 = OFF | | |
| - 3 = OFF | | |
| - 4 = Not Used. | | |
| 08/05/95 DIP Switches verified to be correct. Both DA001's. | | |

IV. SUBROUTINE & SCREEN BIT CROSS REFERENCE

| SUBROUTINE | # | SCREEN # | TITLE | LAMP NUM DISP TOUCH SW | BIT | WORD | |
|---|---|---|---|---|---|---|---|
| Start-Up | 000 | 1 | Introd'n | Enter | 30000 | — | 30000 |
| Start-Up | 000 | 2 | AB. Shutdown | Times-Out | — | — | 30000 |
| Start-Up | 000 | 3 | Start Mode | Begin | 30205 SWSC3? | — | 30000 |
| Start-Up | 000 | 3 | Start Mode | Resume | 30203 | — | 30000 |
| Start-Up | 000 | 4 | Warm-Up | Times-Out | — | — | 30000 |
| Change Para. | 001 | 5 | Change Para. | Yes | SWSC6 | — | 30001 |
| Change Para. | 001 | 5 | Change Para. | No | 30002 | — | 30001 |
| Change Para. | 001 | 6 | Chg. Seal Force | Yes | SWSC7 | — | 30001 |
| Change Para. | 001 | 6 | Chg. Seal Force | No | SWSC9 | — | 30001 |
| Change Para. | 001 | 7 | Set Seal Force | Enter | SWSC8 | — | 30001 |
| Change Para. | 001 | 7 | Set Seal Force | Keypad | — | DM0000 | 30001 |
| Change Para. | 001 | 8 | Confirm Seal Force | Yes | SWSC9 | — | 30001 |
| Change Para. | 001 | 8 | Confirm Seal Force | No | SWSC7 | — | 30001 |
| Change Para. | 001 | 9 | Chg. ST Evac Press | Yes | SWSC10 | — | 30001 |
| Change Para. | 001 | 9 | Chg. ST Evac Press | No | SWSC12 | — | 30001 |
| Main | | | | | 30204 (HR00)CMP=32 | — | |
| Change Para. | 001 | 10 | Set ST Evac Press | Enter | SWSC11 | — | 30001 |
| Change Para. | 001 | 10 | Set ST Evac Press | Keypad | — | DM0001 | 30001 |
| Change Para. | 001 | 11 | Confirm ST. Evac Press | Yes | SWSC12 | — | 30001 |
| Change Para. | 001 | 11 | Confirm ST. Evac Press | No | SWSC10 | — | 30001 |
| Change Para. | 001 | 11 | Confirm ST. Evac Press | Num Disp | 1/002/Di | — | 30001 |
| Change Para. | 001 | 12 | Chg. Drum Evac Press | Yes | SWSC13 | — | 30001 |
| Change Para. | 001 | 12 | Chg. Drum Evac Press | No | SWSC15 | — | 30001 |
| Change Para. | 001 | 12 | Chg. Drum Evac Press | Num Disp | 1/003/Di | — | 30001 |
| Change Para. | 001 | 13 | Set Drum Evac Press | Enter | SWSC14 | — | 30001 |
| Change Para. | 001 | 13 | Set Drum Evac Press | Key Pad | — | — | 30001 |
| Change Para. | 001 | 14 | Confirm Drum | Yes | SWSC15 | — | 30001 |

-continued

IV. SUBROUTINE & SCREEN BIT CROSS REFERENCE

| SUBROUTINE | # | SCREEN # | TITLE | LAMP NUM DISP TOUCH SW | BIT | WORD | |
|---|---|---|---|---|---|---|---|
| Change Para. | 001 | 14 | Evac Press Confirm Drum | No | SWSCI3 | — | 30001 |
| Change Para. | 001 | 14 | Evac Press Confirm Drum | Num Disp | 1/003/Di | — | 30001 |
| Change Para. | 001 | 15 | Evac Press Change Drum Purge Press | Yes | SWSC16 | — | 30001 |
| Change Para. | 001 | 15 | Change Drum Purge Press | No | SWSC18 | — | 30001 |
| Change Para. | 001 | 15 | Change Drum Purge Press | Num Disp | 1/004/Di | — | 30001 |
| Change Para. | 001 | 16 | Set Drum Purge | Enter | SWSC17 | — | 3000 |
| Change Para. | 001 | 16 | Set Drum Purge | Num Disp | 1/004/Di | — | 3000 |
| Change Para. | 001 | 17 | Confirm Drum Purge | Yes | SWSC18 | — | 3000 |
| Change Para. | 001 | 17 | Confirm Drum Purge | No | SWSC16 | — | 3000 |
| Change Para. | 001 | 17 | Confirm Drum Purge | Num Disp | 1/004/Di | — | 3000 |
| Change Para. | 001 | 18 | Change Cabinet Diff PR | Yes | SWSC19 | — | 3000 |
| Change Para. | 001 | 18 | Change Cabinet Diff PR | No | SWSC21 | — | 3000 |
| Change Para. | 001 | 18 | Change Cabinet Diff PR | Num Disp | 1/005/Di | — | 3000 |
| Change Para. | 001 | 19 | Set Cabinet Diff PR | Enter | SWSC20 | — | 3000 |
| Change Para. | 001 | 19 | Set Cabinet Diff PR | Keypad | 1/005/Di | — | 3000 |
| Change Para. | 001 | 20 | Confirm Cabinet Diff PR | Yes | SWSC11 | — | 3000 |
| Change Para. | 001 | 20 | Confirm Cabinet Diff PR | No | SWSC19 | — | 3000 |
| Change Para. | 001 | 20 | Confirm Cabinet Diff PR | Num Disp | 1/005/Di | — | 3000 |
| Change Para. | 001 | 21 | Change In. Object Force | Yes | SWSC22 | — | 3000 |
| Change Para. | 001 | 21 | Change In. Object Force | No | SWSC24 | — | 3000 |
| Change Para. | 001 | 21 | Change In. Object Force | Num Disp | 1/006/Di | — | 3000 |
| Change Para. | 001 | 22 | Set In. Object Force | Enter | SWSW23 | — | 3000 |
| Change Para. | 001 | 22 | Set In. Object Force | Keypad | 1/006/Di | — | 3000 |
| Change Para. | 001 | 23 | Confirm In. Object | Yes | 30002 | — | 30001 |
| Change Para. | 001 | 23 | Confirm In. Object | No | SWSC22 | — | 30001 |
| Change Para. | 001 | 23 | Confirm In. Object | Num Disp | 1/006/Di | — | 30001 |
| Insert Filter | 002 | 24 | Insert Standard Filter | Ready | 30003 | — | 30002 |
| Load Drum | 003 | 25 | Load Drum | Ready | 30004 | — | 30003 |
| Load Drum | 003 | 26 | Load Drum Errors | Access Door Open | 000001 | — | 30003 |
| Load Drum | 003 | 26 | Load Drum Errors | Cabinet Door Open | 000000 | — | 30003 |
| Load Drum | 003 | 26 | Load Drum Errors | Drum In Cabinet | 000002 | — | 30003 |
| Initial 1 | 004 | 27 | In Progress | Times-Out | — | — | 30004 |
| Initial 2 | 005 | 28 | System Initialization | Enter | 30006 | — | 30005 |
| Weigh Drum 1 | 006 | 29 | Weigh Drum | Weigh | 30007 | — | 30006 |
| Weigh Drum 2 | 007 | 30 | In Progress | Times-Out | — | — | 30007 |
| Weigh Drum 3 | 008 | 31 | Drum Weighed | Raise | 30009 | — | 30008 |
| Weigh Drum 3 | 008 | 32 | Excessive Drum Weight | Abort | 30111 | — | 30008 |
| Weigh Drum 3 | 008 | 33 | Weigh Drum Time-Out | Retry | 30006 | — | 30008 |
| Weigh Drum 3 | 008 | 33 | Weigh Drum Time-Out | Abort | 30111 | — | 30008 |
| Raise/Seal 1 | 009 | 34 | In Progress | Times-Out | — | — | 30009 |
| Raise/Seal 2 | 010 | 35 | Raise Seal Drum 2 | Lower | 30011 | — | 30010 |
| Raise/Seal 2 | 010 | 35 | Raise Seal Drum 2 | Seal Force Num Disp | — | 1/000/Di | 30010 |
| Raise/Seal 2 | 010 | 36 | Raise/Seal Error 1 | Abort | 30111 | — | 30010 |
| Lower Ph 1 | 011 | 37 | *In Progress | Times-Out | — | — | 30011 |
| Lower Ph 2 | 012 | 38 | Powerhead Lowered | Seal | 30013 | — | 30012 |
| Lower Ph 2 | 012 | 38 | Powerhead Lowered | Install | 30106 | — | 30012 |
| Lower Ph 2 | 012 | 39 | Lower Ph Error 1 | Retract | 30108 | — | 30012 |
| Seal Test 1 | 013 | 40 | Seal Test 1 | Times-Out | — | — | 30013 |
| Seal Test 2 | 014 | 41 | Seal Test 2 | Bore | SWSC44 | — | 30014 |
| Seal Test 2 | 014 | 42 | Seal Test Error 1 | Retry | SWSC43 | — | 30014 |
| Seal Test 2 | 014 | 42 | Seal test Error 1 | Abort | 30111 | — | 30014 |
| Seal Test 2 | 014 | 43 | Seal Test Retry | Lower | 30111 | — | 30014 |
| Seal Test 2 | 014 | 43 | Seal Test Retry | Retract | 30108 | — | 30014 |
| Seal Test 2 | 014 | 44 | Confirm Data Acquisition | Bore | 30015 | — | 30014 |
| Bore/Sample 1 | 015 | 45 | Bore to Sample Depth | Force Num Disp | — | 1/010/Di | 30015 |
| Bore/Sample 1 | 015 | 45 | Bore to Sample Depth | Min Num Disp | — | 1/011/Di | 30015 |
| Bore/Sample 1 | 015 | 45 | Bore to Sample Depth | Sec Num Disp | — | 1/012/Di | 30015 |
| Bore/Sample 2 | 016 | 46 | Bore Completed | Sample | 30101 | — | 30100 |
| Bore/Sample 2 | 016 | 47 | Bore/Sample Error 1 | Retract | 30108 | — | 30100 |

-continued

IV. SUBROUTINE & SCREEN BIT CROSS REFERENCE

| SUBROUTINE | # | SCREEN # | TITLE | LAMP TOUCH SW | BIT | NUM DISP BIT | WORD |
|---|---|---|---|---|---|---|---|
| Sample 1 | 017 | 48 | S/Analysis I | Minutes Num Disp | — | 1/013/Di | 30101 |
| Sample 1 | 017 | 49 | Analysis Done | Evacuate | 30102 | — | 30101 |
| Sample 1 | 017 | 49 | Analysis Done | Install | 30106 | — | 30101 |
| Sample 1 | 017 | 50 | S/Analysis Error 1 | Evacuate | 30102 | — | 30101 |
| Sample 1 | 017 | 50 | S/Analysis Error 1 | Retry | 30106 | — | 30101 |
| Sample 1 | 017 | 50 | S/Analysis Error 1 | Install | 30201 | — | 30101 |
| Evacuate 1 | 018 | 51 | Evacuate 1 | Pressure Num Disp | — | 1/000/Di | 30102 |
| Evacuate 1 | 018 | 51 | Evacuate 1 | Minutes Num Disp | — | 1/014/Di | 30102 |
| Evacuate 1 | 018 | 51 | Evacuate 1 | Seconds Num Disp | — | 1/015/Di | 30102 |
| Evacuate 2 | 019 | 52 | Evacuate 2 | Pressure Num Disp | — | 1/000/Di | 30103 |
| Evacuate 2 | 019 | 52 | Evacuate 2 | Purge | 30104 | — | 30103 |
| Purge 1 | 020 | 53 | Purge 1 | Pressure Num Disp | — | 1/000/Di | 30104 |
| Purge 1 | 020 | 53 | Purge 1 | Minutes Num Disp | — | 1016/Di | 30104 |
| Purge 1 | 020 | 53 | Purge 1 | Seconds Num Disp | — | 1/017/Di | 30104 |
| Purge 2 | 021 | 54 | Purge 2 | Pressure Num Disp | — | 1/000/Di | 30105 |
| Purge 2 | 021 | 54 | Purge 2 | Evacuate | 30102 | — | 30105 |
| Purge 2 | 021 | 54 | Purge 2 | Sample | 30101 | — | 30105 |
| Inst Filter 1 | 022 | 55 | Inst Filter 1 | Inst Filter 1 | Times-Out | — | 30106 |
| Install Filter 2 | 023 | 56 | Inst Filter 2 | Retract | 30108 | — | 30107 |
| Install Filter 2 | 023 | 57 | Error 1 F | Retract | 30108 | — | 30107 |
| Install Filter 2 | 023 | 58 | Error 2 F | Retract | 30108 | — | 30107 |
| Install Filter 2 | 023 | 59 | Install Stub Filter F | Abort | 30108 | — | 30107 |
| Retract Ph 1 | 024 | 60 | Retract Ph 1 | Times-Out | — | — | 30108 |
| Retract Ph 2 | 025 | 61 | Retract Ph 2 | Continue | 30109 | — | 30109 |
| Retract Ph 2 | 025 | 62 | Seal Test Abort | Abort | 30111 | — | 30109 |
| Retract Ph 2 | 025 | 63 | Stub Filter Inst Time-Out | Abort | 3011I | — | 30109 |
| Retract Ph 2 | 025 | 64 | Seal Test Retry | Abort | 30111 | — | 30109 |
| Retract Ph 2 | 025 | 65 | In. Pene Obj Time-Out | Stub | 30110 | — | 30109 |
| Insert Stub Fil | 026 | 66 | Stub Filter Insertion | Install | 30106 | — | 30110 |
| Lower Drum 1 | 027 | 67 | Lower Drum 1 | Times-Out | — | — | 30111 |
| Lower Drum 2 | 028 | 68 | Lower Drum 2 | Survey | 30113 | — | 30112 |
| Lower Drum 2 | 028 | 68 | Lower Drum 2 | Continue | SWSC6 | — | 30112 |
| Lower Drum 2 | 028 | 69 | Seal Test Retry | Raise | 30009 | — | 30112 |
| Survey 1 | 029 | 70 | Survey Drum Lid | Unload | 30114 | — | 30013 |
| Survey 1 | 029 | 70 | Survey Drum Lid | Lamp-Ready | DM001800 | — | 30013 |
| Unload Drum 1 | 030 | 71 | Unload Drum 1 | Times-Out | — | — | 30114 |
| Unload Drum 2 | 031 | 72 | Unload Drum 2 | Exit | 30200 | — | 30115 |
| Unload Drum 2 | 031 | 72 | Unload Drum 2 | Continue | 30001 | — | 30115 |
| Unload Drum 2 | 031 | 73 | Stub Filter Man. Inst. Instr. | Continue | SWSC74 | — | 30115 |
| Exit | 032 | 74 | Exit | Operator Turns Off | 032 → HR00 Screen 74 → HrDi | — | 30200 |
| Initialize 2 | 005 | 75 | System Init Error 1 | Abort | 30115 | — | 30005 |
| Lower Ph 2 | 012 | 76 | L Drive Move Time-Out | Abort | 30206 | — | 30012 |
| Install Fil 2 | 023 | 76 | L Drive Move Time-Out | Abort | 30206 | — | 30107 |
| Retract Ph 2 | 025 | 76 | L Drive Move Time-Out | Abort | 30206 | — | 30109 |
| Bore to Sample 2 | 016 | 76 | L Drive Move Time-Out | Abort | 30206 | — | 30100 |
| Seal Test Abort | | 50704 | Retract 2 | uses to display screen | — | | |
| Stub Fil Time-Out | | 50703 | Retract 2 | uses to display screen | — | | |
| Seal Test Retry | | 50702 | Retract 2 | uses to display screen | — | | |
| Impene. Obj. | | 50701 | Retract 2 | uses to display screen | — | | |

8.0 Activating DVSLSSlO or CALIBLSS

Assuming the auxiliary personal computer (APC) is located within 10 feet of the PLC and/or NT20M Programmable Terminal Touch Screen (TS), is powered, turned ON, and displaying the "C" prompt, do the following:

1. Type CD/LSS, <ENTER>. Execution will switch to the LSS directory.

2. Type LSS. The LSS program will activate and the SETUP Menu will be displayed.
3. If it is desired that DVSLSSIO or CALIBLSS be retrieved from a 3.5 inch floppy in drive A of the auxiliary computer, press the up arrow key until the DATA DISK Drive Menu item is highlighted. Press <ENTER>, then press the letter A, and <ENTER> again. LSS will now "look at" drive A.
4. If the program version resident on the C: drive is desired, omit step three.
5. Move cursor to Program and Press <ENTER>.
6. Press END key to bring up menu, then select "Clean Memory", <ENTER>, then Yes.
7. Press END key to bring up menu, move cursor to Retrieve Program, Press <ENTER>.
8. Type in program name, DVSLSSIO or CALIBLSS
9. Press (Control, O) to get soft function keys displayed at screen bottom as: F1 "PCON"
10. If PLC on, the soft function keys at screen bottom will changeto: 1. "Cancel", 2. "SU . . . ", indicating connection was made.
11. Press END key to bring up menu, move cursor to transfer program, press <ENTER>.
12. Sub menu comes up, move cursor to "Computer=>PC", Press <ENTER>.
13. New menu comes up, select "Send to END", Press <ENTER>.
14. Cycle power, program now ready and loaded.
15. Control O, F4"PERM".
16. Control O, F2"RUN".
17. Control O, F1.
18. End cursor to Setup, <ENTER>, select EXIT TO DOS, Y <ENTER>.

TO DOWNLOAD SCREENS USING NTM SUPPORT TOOL Version 4.2
1. Connect serial cable from comm port 1 on auxiliary computer to Touch Screen Fare.
2. C:CD NT, then enter
3. NTM
4. Move cursor to TRU DVS 2
5. Go to touch screen, press top 3 keys simultaneously
6. Hit F6 to transmit
7. Confirm: Yes
8. Verify: No
9. Transmit data with deleting (Spacebar)
10. Return
11. Escape OPERATING INSTRUCTIONS
10. Making Changes to LINEAR DRIVE Program
1. Connect gray serial communication cable from linear driveto Comm Port #1 of auxiliary computer (AC).
2. If LSS program is active on AC, press END key. A pop-up menu will appear.
3. Press thet ↑ arrow key to highlight header menu at thetop of screen.
4. Move cursor laterally until "Setup" is highlighted. Then press ENTER.
5. Press "M", then press "Y". This will cause execution to Exit LSS.
6. CD/XWARE, then XWARE This will activatethe linear drive program.
7. Click on "File".
8. Click on "Open".
9. Click on DVSlong. PRG.
10. Make changes to program. (Caution: Requires expert system knowledge)
11. Save.
12. Click on terminal, click on connect, <ENTER> to get>prompt.
13. Enter RIFS, Then press ENTER.
14. FILE, OPEN, DVS LONG, PRG
15. Click on UTILITY. Then click on DOWNLOAD.
16. When Download complete, must cycle power.
17. Change cable in back of AC to PLC Cable, if desired.
11. CHANGING FROM CALIBLSS TO DVSLSS10 OR VICE VERSA
1. If PLC is running, press CTRL/O. Then press F4, then enter "Y".
2. Execution will switch.

From the foregoing description, one skilled in the art can easily ascertain the essential characteristics of this invention, and without departing from the spirit and scopethereof, can make various changes and modifications of the invention to adapt it to various usages and conditions.

What is claimed is:
1. A method for testing gas accumulating in the headspace of a drum comprising:
   isolating the drum from the surrounding environment in an enclosed first space;
   sealing with a seal a portion of the drum's surface proximate the headspace thereof to form a sealed surface portion isolated from the first enclosed space while providing access to the sealed surface portion of the drum surface from a second enclosed space through a third space in the seal, wherein the second enclosed space is radially spaced from and positioned around the seal to enclose and provide access to tooling having portions axially spaced from and portions axially aligned with and receivable through the seal;
   closing the third space;
   evacuating air from the third spaceto form a vacuum therein;
   by using the tooling, boring a hole through the sealed surface portion of the drum to release gases from the headspace into the third space;
   analyzing the gases with a gas chromatograph connected to a mass spectrometer to identify and quantify the make up of total volatile organic compounds present in the drum;
   purging the gases in the headspace if the gases are considered dangerous; and
   installing a filter in the hole bored through the sealed surface portion of the drum for venting the drum.
2. The method of claim 1 further comprising testing the vacuum in the third space and reforming the vacuum if the vacuum is inadequate.
3. The method of claim 2 further including:
   weighing the drum prior to sealing the sealed surface portion; and
   pushing the drum into sealing engagement with a gasket on the seal by exerting a force on the drum greater than the weight of the drum.
4. The method of claim 3, wherein the boring is performed by rotating a cutting bit portion of a filter/cutter assembly which comprises the tooling at a first relatively high speed while lowering the cutting bit to create the hole through the sealed surface portion; and subsequently
   rotating the filter/cutter assembly at a relatively slow speed to self-tap the filter/cutter assembly in the hole.

5. The method of claim 4 further including withdrawing the filter/cutter assembly from the third space if the cutter encounters an impenetrable object and replacing the filter/cutter with a filter having a relatively short threaded shank for tapping.

6. The method of claim 5, wherein the drum contains radioactive waste and wherein the gases being analyzed are combustible gases, including possibly hydrogen, methane and volatile organic compounds released from the waste.

7. The method of claim 6 further comprising continuously introducing fresh air into the first and second spaces, continuously withdrawing the fresh air therefrom and filtering the fresh air before discharging it into the atmosphere.

8. The method of claim 5, wherein the drum includes a lid and wherein the sealed surface portion through which the bore is made and through which the vent inserted is a surface of the lid.

9. The method of claim 5 further including displaying indicia indicative of the steps on a touch-screen terminal and touching the screen to move from step to step.

10. The method of claim 1 further including:

weighing the drum prior to sealing the sealed surface portion; and pushing the drum into sealing engagement with a gasket on the seal by exerting a force on the drum greater than the weight of the drum.

11. The method of claim 1, wherein the boring is performed by rotating a cutting bit portion of a filter/cutter assembly at a first relatively high speed while lowering the cutting bit to create the hole through the sealed surface portion; and subsequently rotating the filter/cutter assembly at a relatively slow speed to self-tap the filter/cutter assembly in the hole.

12. The method of claim 11 further including withdrawing the filter/cutter assembly from the third space if the cutter encounters an impenetrable object and replacing the filter/cutter with a filter having a relatively short threaded shank for tapping.

13. The method of claim 1, wherein the drum includes a lid and wherein the sealed surface portion through which the bore is made and through which the vent inserted is a surface of the lid.

14. The method of claim 5 further including displaying indicia indicative of the steps on a touch-screen terminal and touching the screen to move from step to step.

15. The method of claim 1 further including displaying indicia indicative of the steps on a touch-screen terminal and touching the screen to move from step to step.

16. Apparatus for testing and venting headspace gases in drums containing stored material, the apparatus comprising:

a drug containment cabinet for isolating the drum from the environment;

a power head chamber above the drum containment chamber for containing a power head for applying rotational and axial motion to a filter/cutter assembly detachably mounted on the power head; the filter cutter/outer assembly adapted to provide a vent in the drum, a sealing assembly connecting the drum chamber to the power head chamber, the sealing assembly being aligned with the filter/cutter assembly when the filter/cutter assembly is mounted in the power head, and the sealing assembly including a vacuum line for connecting the hollow core of the sealing assembly to a vacuum source;

a lift in the drum containment chamber for lifting the drum into sealing engagement with the first end of the sealing assembly to isolate a portion of the drum lid from the drum containment chamber while exposing that portion of the drum lid to the filter/cutter assembly of the power head located in the power head chamber;

a closure device on the power head for sealing a second end of the sealing assembly when the filter/cutter assembly is inserted therein by the power head to create a vacuum chamber withing the sealing assembly;

a vacuum pump attached to the vacuum line of the sealing assembly for evacuating the vacuum chamber; and a gas analyzer connected to the vacuum line for analyzing gas drawn into the vacuum chamber created within the sealing assembly upon puncturing the drum with the filter/cutter assembly to provide the vent, the gas analyzer including a gas chromatograph connected to a mass spectrometer to identify and quantify the make up of the total volatile organic compounds present in the drum.

17. The apparatus of claim 16, wherein the lift includes a force transducer for weighing the drum and for determining the magnitude of the force with which the drum is urged against the sealing assembly.

18. The apparatus of claim 16, wherein the power head chamber is a glovebox.

19. The apparatus of claim 16 further including an air handling system for exhausting air from the drum containment chamber and the power head chamber.

20. The apparatus of claim 16 further including a computerized control system comprising a display subroutine, a control subroutine and a touch screen terminal, thetouch-screen terminal displaying a series of control commands for an operator to initiate by touching the screen of the terminal.

21. The apparatus of claim 16 further including an external manifold connected by a valve to the gas analyzer for sampling gases in drums already having vents.

22. The apparatus of claim 21 wherein the manifold includes a plurality of lines connected to a main line by valves each having an end for coupling with the vent of a single drum.

* * * * *